US008521259B2

(12) United States Patent
Mandrusov et al.

(10) Patent No.: US 8,521,259 B2
(45) Date of Patent: Aug. 27, 2013

(54) AGENTS THAT STIMULATE THERAPEUTIC ANGIOGENESIS AND TECHNIQUES AND DEVICES THAT ENABLE THEIR DELIVERY

(75) Inventors: Evgenia Mandrusov, Campbell, CA (US); Murthy V. Simhambhatla, San Jose, CA (US); Syed Hossainy, Fremont, CA (US); Eugene T. Michal, San Francisco, CA (US); Charles Claude, Santa Clara, CA (US); Jessica G. Chiu, Belmont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1038 days.

(21) Appl. No.: 10/781,984

(22) Filed: Feb. 18, 2004

(65) Prior Publication Data

US 2004/0162516 A1 Aug. 19, 2004

Related U.S. Application Data

(62) Division of application No. 10/011,071, filed on Nov. 30, 2001, now Pat. No. 6,702,744.

(60) Provisional application No. 60/300,042, filed on Jun. 20, 2001.

(51) Int. Cl.
*A61B 5/00* (2006.01)

(52) U.S. Cl.
USPC ........ 600/427; 600/439; 600/476; 604/96.01; 604/103.02; 604/164.03; 604/164.12; 604/264; 604/272; 604/509

(58) Field of Classification Search
USPC ......... 600/439, 427, 476; 604/500, 506–510, 604/96.01, 103.02, 103.06, 93.01, 164.01, 604/164.09–164.12, 264, 272
See application file for complete search history.

(56) References Cited

U.S. PATENT DOCUMENTS 3,780,733 A 12/1973 Martinez-Manzor
4,141,973 A 2/1979 Balazs
(Continued)

FOREIGN PATENT DOCUMENTS

EP 0331584 9/1989
EP 861632 9/1998
(Continued)

OTHER PUBLICATIONS

James M. Anderson, Matthew S. Shive, "Biodegradation and Biocompatibility of PLA and PLGA Microspheres," Advanced Drug Delivery Reviews 28 (1997), pp. 5-24.
(Continued)

*Primary Examiner* — Ruth S Smith
(74) *Attorney, Agent, or Firm* — Randy Shen; Blakely Sokoloff Taylor & Zafman LLP

(57) ABSTRACT

A method including positioning a catheter at a location in a blood vessel; imaging a thickness of a portion of a wall of the blood vessel at the location; identifying a treatment site; advancing a needle a distance into the wall of the blood vessel to the treatment site; and introducing a treatment agent through the needle to the treatment site. A composition including an inflammation-inducing agent and a carrier in the form of microspheres having a particle size suitable for transvascular delivery. A composition including a therapeutic angiogenesis promoter in a carrier and an opsonin-inhibitor coupled to the carrier. An apparatus for delivery of a therapeutic angiogenesis promoter.

32 Claims, 9 Drawing Sheets

(56) References Cited

U.S. PATENT DOCUMENTS

| | | | | |
|---|---|---|---|---|
| 4,617,186 | A | 10/1986 | Schafer et al. | |
| 4,794,931 | A * | 1/1989 | Yock | 600/439 |
| 4,818,291 | A | 4/1989 | Iwatsuki et al. | |
| 5,000,185 | A | 3/1991 | Yock | |
| 5,024,234 | A | 6/1991 | Leary et al. | |
| 5,049,130 | A | 9/1991 | Powell | |
| 5,092,848 | A * | 3/1992 | deCiutiis | 604/170.01 |
| 5,109,859 | A * | 5/1992 | Jenkins | 600/439 |
| 5,116,317 | A | 5/1992 | Carson et al. | |
| 5,128,326 | A | 7/1992 | Balazs et al. | |
| 5,171,217 | A | 12/1992 | March et al. | |
| 5,202,745 | A | 4/1993 | Sorin et al. | |
| 5,203,338 | A * | 4/1993 | Jang | 600/463 |
| 5,270,300 | A | 12/1993 | Hunziker | |
| 5,291,267 | A | 3/1994 | Sorin et al. | |
| 5,306,250 | A | 4/1994 | March et al. | |
| 5,321,501 | A | 6/1994 | Swanson et al. | |
| 5,328,955 | A | 7/1994 | Rhee et al. | |
| 5,336,252 | A | 8/1994 | Cohen | |
| 5,354,279 | A * | 10/1994 | Hofling | 604/164.12 |
| 5,365,325 | A | 11/1994 | Kumasaka et al. | |
| 5,372,138 | A * | 12/1994 | Crowley et al. | 600/463 |
| 5,380,292 | A | 1/1995 | Wilson | |
| 5,437,632 | A | 8/1995 | Engelson | |
| 5,455,039 | A | 10/1995 | Edelman et al. | |
| 5,459,570 | A | 10/1995 | Swanson et al. | |
| 5,464,395 | A * | 11/1995 | Faxon et al. | 604/103.02 |
| 5,465,147 | A | 11/1995 | Swanson | |
| 5,485,486 | A | 1/1996 | Gilhousen et al. | |
| 5,499,630 | A * | 3/1996 | Hiki et al. | 600/461 |
| 5,516,532 | A | 5/1996 | Atala et al. | |
| 5,540,912 | A * | 7/1996 | Roorda et al. | 424/422 |
| 5,546,948 | A * | 8/1996 | Hamm et al. | 600/585 |
| 5,554,389 | A | 9/1996 | Badylak et al. | |
| 5,575,815 | A * | 11/1996 | Slepian et al. | 600/36 |
| 5,580,714 | A | 12/1996 | Polovina | |
| 5,580,856 | A | 12/1996 | Prestrelski et al. | |
| 5,588,432 | A * | 12/1996 | Crowley | 600/439 |
| 5,621,610 | A | 4/1997 | Moore et al. | |
| 5,642,234 | A | 6/1997 | Altman et al. | |
| 5,655,548 | A | 8/1997 | Nelson et al. | |
| 5,667,778 | A | 9/1997 | Atala | |
| 5,672,153 | A * | 9/1997 | Lax et al. | 604/22 |
| 5,676,151 | A * | 10/1997 | Yock | 600/463 |
| 5,693,029 | A | 12/1997 | Leonhardt | |
| 5,722,403 | A | 3/1998 | McGee et al. | |
| 5,725,551 | A * | 3/1998 | Myers et al. | 606/213 |
| 5,740,808 | A | 4/1998 | Panescu et al. | |
| 5,749,915 | A * | 5/1998 | Slepian | 128/898 |
| 5,785,689 | A | 7/1998 | De Toledo et al. | |
| 5,810,885 | A | 9/1998 | Zinger | |
| 5,811,533 | A | 9/1998 | Gold et al. | |
| 5,827,313 | A | 10/1998 | Ream | |
| 5,843,156 | A | 12/1998 | Slepian et al. | |
| 5,874,500 | A | 2/1999 | Rhee et al. | |
| 5,879,713 | A | 3/1999 | Roth et al. | |
| 5,900,433 | A | 5/1999 | Igo et al. | |
| 5,906,934 | A | 5/1999 | Grande et al. | |
| 5,919,449 | A | 7/1999 | Dinsmore | |
| 5,935,160 | A | 8/1999 | Auricchio et al. | |
| 5,939,323 | A | 8/1999 | Valentini et al. | |
| 5,941,868 | A * | 8/1999 | Kaplan et al. | 604/500 |
| 5,957,941 | A | 9/1999 | Ream | |
| 5,968,064 | A | 10/1999 | Selmon et al. | |
| 5,979,449 | A | 11/1999 | Steer | |
| 5,981,568 | A | 11/1999 | Kunz et al. | |
| 5,984,908 | A | 11/1999 | Davis et al. | |
| 5,997,536 | A | 12/1999 | Osswald et al. | |
| 6,022,540 | A | 2/2000 | Bruder et al. | |
| 6,045,565 | A | 4/2000 | Ellis et al. | |
| 6,050,949 | A | 4/2000 | White et al. | |
| 6,051,071 | A | 4/2000 | Charvet et al. | |
| 6,051,648 | A | 4/2000 | Rhee et al. | |
| 6,056,744 | A | 5/2000 | Edwards | 606/41 |
| 6,058,329 | A | 5/2000 | Salo et al. | |
| 6,060,053 | A | 5/2000 | Atala | |
| 6,071,305 | A | 6/2000 | Brown et al. | |
| 6,086,582 | A * | 7/2000 | Altman et al. | 606/41 |
| 6,093,177 | A | 7/2000 | Javier, Jr. et al. | |
| 6,099,563 | A | 8/2000 | Zhong | |
| 6,099,864 | A | 8/2000 | Morrison et al. | |
| 6,102,887 | A | 8/2000 | Altman | |
| 6,102,904 | A * | 8/2000 | Vigil et al. | 604/500 |
| 6,102,926 | A | 8/2000 | Tartaglia et al. | |
| 6,120,520 | A * | 9/2000 | Saadat et al. | 606/170 |
| 6,120,904 | A | 9/2000 | Hostettler et al. | |
| 6,127,448 | A | 10/2000 | Domb | |
| 6,133,231 | A | 10/2000 | Ferrara et al. | |
| 6,134,003 | A | 10/2000 | Tearney et al. | |
| 6,151,525 | A | 11/2000 | Soykan | |
| 6,152,141 | A * | 11/2000 | Stevens et al. | 128/898 |
| 6,153,428 | A | 11/2000 | Gustafsson et al. | |
| 6,159,443 | A | 12/2000 | Hallahan | |
| 6,175,669 | B1 | 1/2001 | Colston et al. | |
| 6,177,407 | B1 | 1/2001 | Rodgers et al. | |
| 6,179,809 | B1 * | 1/2001 | Khairkhahan et al. | 604/95.04 |
| 6,183,432 | B1 | 2/2001 | Milo | |
| 6,183,444 | B1 | 2/2001 | Glines et al. | |
| 6,187,330 | B1 | 2/2001 | Wang et al. | |
| 6,190,353 | B1 * | 2/2001 | Makower et al. | 604/95.01 |
| 6,191,144 | B1 * | 2/2001 | Isner | 514/315 |
| 6,192,271 | B1 | 2/2001 | Hayman | |
| 6,193,763 | B1 | 2/2001 | Mackin | |
| 6,197,324 | B1 | 3/2001 | Crittenden | |
| 6,201,608 | B1 | 3/2001 | Mandella et al. | |
| 6,206,893 | B1 | 3/2001 | Klein et al. | |
| 6,206,914 | B1 | 3/2001 | Soykan et al. | |
| 6,207,180 | B1 * | 3/2001 | Ottoboni et al. | 424/426 |
| 6,210,392 | B1 * | 4/2001 | Vigil et al. | 604/507 |
| 6,217,527 | B1 * | 4/2001 | Selmon et al. | 600/585 |
| 6,217,554 | B1 * | 4/2001 | Green | 604/164.01 |
| 6,221,049 | B1 * | 4/2001 | Selmon et al. | 604/164.13 |
| 6,231,546 | B1 * | 5/2001 | Milo et al. | 604/164.13 |
| 6,235,000 | B1 * | 5/2001 | Milo et al. | 604/164.01 |
| 6,241,710 | B1 | 6/2001 | Van Tassel et al. | |
| 6,251,104 | B1 | 6/2001 | Kesten et al. | |
| 6,283,947 | B1 | 9/2001 | Mirzaee | |
| 6,287,285 | B1 | 9/2001 | Michal et al. | |
| 6,290,729 | B1 * | 9/2001 | Slepian et al. | 623/23.72 |
| 6,296,602 | B1 * | 10/2001 | Headley | 494/37 |
| 6,299,604 | B1 | 10/2001 | Ragheb et al. | |
| 6,309,370 | B1 | 10/2001 | Haim et al. | |
| 6,312,725 | B1 | 11/2001 | Wallace et al. | |
| 6,315,994 | B2 | 11/2001 | Usala et al. | |
| 6,323,278 | B2 | 11/2001 | Rhee et al. | |
| RE37,463 | E | 12/2001 | Altman | |
| 6,328,229 | B1 | 12/2001 | Duronio et al. | |
| 6,333,194 | B1 | 12/2001 | Levy et al. | |
| 6,334,872 | B1 | 1/2002 | Termin et al. | |
| 6,338,717 | B1 * | 1/2002 | Ouchi | 600/462 |
| 6,346,098 | B1 | 2/2002 | Yock et al. | |
| 6,346,099 | B1 | 2/2002 | Altman | |
| 6,346,515 | B1 | 2/2002 | Pitaru et al. | |
| 6,358,247 | B1 | 3/2002 | Altman et al. | |
| 6,358,258 | B1 | 3/2002 | Arcia et al. | |
| 6,360,129 | B1 | 3/2002 | Ley et al. | |
| 6,368,285 | B1 | 4/2002 | Osadchy et al. | |
| 6,371,935 | B1 | 4/2002 | Macoviak et al. | |
| 6,371,992 | B1 | 4/2002 | Tanagho et al. | |
| 6,379,379 | B1 | 4/2002 | Wang | |
| 6,385,476 | B1 | 5/2002 | Osadchy et al. | |
| 6,391,052 | B2 | 5/2002 | Buirge et al. | |
| 6,395,023 | B1 | 5/2002 | Summers | |
| 6,409,716 | B1 | 6/2002 | Sahatjian et al. | |
| 6,416,510 | B1 | 7/2002 | Altman et al. | |
| 6,432,119 | B1 * | 8/2002 | Saadat | 606/170 |
| 6,436,135 | B1 | 8/2002 | Goldfarb | |
| 6,440,947 | B1 | 8/2002 | Barron et al. | |
| 6,443,941 | B1 | 9/2002 | Slepian et al. | |
| 6,443,949 | B2 | 9/2002 | Altman | |
| 6,447,504 | B1 | 9/2002 | Ben-Haim et al. | |
| 6,458,095 | B1 | 10/2002 | Wirt et al. | |
| 6,458,098 | B1 | 10/2002 | Kanesaka | |
| 6,464,862 | B2 | 10/2002 | Bennett et al. | |

| | | | |
|---|---|---|---|
| 6,465,001 B1 * | 10/2002 | Hubbell et al. | 424/423 |
| 6,478,776 B1 | 11/2002 | Rosenman et al. | |
| 6,482,231 B1 | 11/2002 | Abatangelo et al. | |
| 6,485,481 B1 | 11/2002 | Pfeiffer | |
| 6,494,862 B1 * | 12/2002 | Ray et al. | 604/96.01 |
| 6,514,217 B1 * | 2/2003 | Selmon et al. | 600/585 |
| 6,548,081 B2 | 4/2003 | Sadozai et al. | |
| 6,554,801 B1 * | 4/2003 | Steward et al. | 604/164.03 |
| 6,599,267 B1 | 7/2003 | Ray et al. | |
| 6,602,241 B2 * | 8/2003 | Makower et al. | 604/509 |
| 6,624,245 B2 | 9/2003 | Wallace et al. | |
| 6,628,988 B2 | 9/2003 | Kramer et al. | |
| 6,629,947 B1 | 10/2003 | Sahatjian et al. | |
| 6,632,457 B1 | 10/2003 | Sawhney | |
| 6,635,267 B1 | 10/2003 | Miyoshi et al. | |
| 6,660,034 B1 | 12/2003 | Mandrusov et al. | |
| 6,682,730 B2 | 1/2004 | Mickle et al. | |
| 6,689,608 B1 | 2/2004 | Mikos et al. | |
| 6,692,466 B1 | 2/2004 | Chow et al. | |
| 6,702,744 B2 | 3/2004 | Mandrusov et al. | |
| 6,706,034 B1 | 3/2004 | Bhat | |
| 6,726,677 B1 * | 4/2004 | Flaherty et al. | 604/528 |
| 6,737,072 B1 | 5/2004 | Angele et al. | |
| 6,748,258 B1 | 6/2004 | Mueller et al. | |
| 6,749,617 B1 | 6/2004 | Palasis et al. | |
| 6,759,431 B2 | 7/2004 | Hunter et al. | |
| 6,761,887 B1 | 7/2004 | Kavalkovich et al. | |
| 6,777,000 B2 | 8/2004 | Ni et al. | |
| 6,777,231 B1 | 8/2004 | Katz et al. | |
| 6,790,455 B2 | 9/2004 | Chu et al. | |
| 6,858,229 B1 | 2/2005 | Hubbell et al. | |
| 6,916,648 B2 | 7/2005 | Goddard et al. | |
| 6,992,172 B1 | 1/2006 | Chang et al. | |
| 7,112,587 B2 | 9/2006 | Timmer et al. | |
| 7,129,210 B2 | 10/2006 | Lowinger et al. | |
| 7,169,127 B2 | 1/2007 | Epstein et al. | |
| 7,273,469 B1 | 9/2007 | Chan et al. | |
| 7,374,774 B2 | 5/2008 | Bowlin et al. | |
| 7,615,373 B2 | 11/2009 | Simpson et al. | |
| 7,732,190 B2 | 6/2010 | Michal et al. | |
| 7,815,590 B2 | 10/2010 | Cooper | |
| 8,192,760 B2 | 6/2012 | Hossainy et al. | |
| 2001/0023349 A1 | 9/2001 | Van Tassel et al. | |
| 2001/0055615 A1 | 12/2001 | Wallace et al. | |
| 2002/0013408 A1 | 1/2002 | Rhee et al. | |
| 2002/0042473 A1 | 4/2002 | Trollsas et al. | |
| 2002/0072706 A1 | 6/2002 | Hiblar et al. | |
| 2002/0076441 A1 | 6/2002 | Shih et al. | |
| 2002/0090725 A1 | 7/2002 | Simpson et al. | |
| 2002/0102272 A1 | 8/2002 | Rosenthal et al. | |
| 2002/0124855 A1 | 9/2002 | Chachques | |
| 2002/0131974 A1 * | 9/2002 | Segal | 424/184.1 |
| 2002/0142458 A1 | 10/2002 | Williams et al. | |
| 2002/0146557 A1 | 10/2002 | Claude et al. | |
| 2002/0188170 A1 | 12/2002 | Santamore et al. | |
| 2003/0023202 A1 | 1/2003 | Nielson | |
| 2003/0040712 A1 | 2/2003 | Ray et al. | |
| 2003/0050597 A1 | 3/2003 | Dodge et al. | |
| 2003/0078671 A1 | 4/2003 | Lesniak et al. | |
| 2003/0105493 A1 | 6/2003 | Salo | |
| 2003/0175410 A1 | 9/2003 | Campbell et al. | |
| 2004/0002650 A1 | 1/2004 | Mandrusov et al. | |
| 2004/0181206 A1 | 9/2004 | Chiu et al. | |
| 2004/0185084 A1 | 9/2004 | Rhee et al. | |
| 2004/0208845 A1 | 10/2004 | Michal et al. | |
| 2004/0213756 A1 | 10/2004 | Michal et al. | |
| 2005/0015048 A1 | 1/2005 | Chiu et al. | |
| 2005/0031874 A1 | 2/2005 | Michal et al. | |
| 2005/0042254 A1 | 2/2005 | Freyman et al. | |
| 2005/0065281 A1 | 3/2005 | Lutolf et al. | |
| 2005/0070844 A1 | 3/2005 | Chow et al. | |
| 2005/0186240 A1 | 8/2005 | Ringeisen et al. | |
| 2005/0281883 A1 | 12/2005 | Daniloff et al. | |
| 2006/0149392 A1 | 7/2006 | Hsieh et al. | |
| 2006/0233850 A1 | 10/2006 | Michal | |
| 2007/0270948 A1 | 11/2007 | Wuh | |
| 2008/0025943 A1 | 1/2008 | Michal et al. | |
| 2012/0225040 A1 | 9/2012 | Hossainy et al. | |
| 2012/0225041 A1 | 9/2012 | Hossainy et al. | |

FOREIGN PATENT DOCUMENTS

| | | |
|---|---|---|
| EP | 938871 | 9/1999 |
| GB | 2194144 | 3/1988 |
| JP | 61205446 | 9/1986 |
| JP | 06507106 | 8/1994 |
| JP | 10236984 | 9/1998 |
| JP | 2000262525 | 9/2000 |
| JP | 2003062089 | 3/2003 |
| WO | WO-9210142 | 6/1992 |
| WO | WO-9315781 | 8/1993 |
| WO | WO-9830207 | 7/1998 |
| WO | WO-9854301 | 12/1998 |
| WO | WO-9953943 | 10/1999 |
| WO | WO-0016818 | 3/2000 |
| WO | WO-0054661 | 9/2000 |
| WO | WO-0071196 | 11/2000 |
| WO | WO-0124775 | 4/2001 |
| WO | WO-0124842 | 4/2001 |
| WO | WO-0145548 | 6/2001 |
| WO | WO-0149357 | 7/2001 |
| WO | WO-0200173 | 1/2002 |
| WO | WO-0204008 | 1/2002 |
| WO | WO-0228450 | 4/2002 |
| WO | WO-0240070 | 5/2002 |
| WO | WO-02072166 | 9/2002 |
| WO | WO-02087623 | 11/2002 |
| WO | WO-03022324 | 3/2003 |
| WO | WO-03022909 | 3/2003 |
| WO | WO-03026492 | 4/2003 |
| WO | WO-03027234 | 4/2003 |
| WO | WO-03064637 | 8/2003 |
| WO | WO-04000915 | 12/2003 |
| WO | WO-2004050013 | 6/2004 |
| WO | WO-2004066829 | 8/2004 |
| WO | WO-20040091592 | 10/2004 |
| WO | WO-2004098669 | 11/2004 |
| WO | WO-2005061019 | 7/2005 |
| WO | WO-2005067890 | 7/2005 |
| WO | WO-2006039704 | 4/2006 |
| WO | WO-2006113407 | 10/2006 |
| WO | WO-2007048831 | 3/2007 |
| WO | WO-2007145909 | 12/2007 |

OTHER PUBLICATIONS

I. Buschmann, W. Schaper, "Arteriogenesis Versus Angiogenesis: Two Mechanisms of Vessel Growth," News Physiol. Sci., vol. 14, Jun. 1999, pp. 121-125.

Michael J. Caplan, et al., "Dependence on pH of Polarized Sorting of Secreted Proteins," Dept. of Cell Biology and Dept. of Pathology, Yale University School of Medicine, Nature vol. 329, Oct. 15, 1987, p. 630.

A. Helisch, W. Schaper, "Angiogenesis and Arteriogenesis—Not Yet for Prescription," Neue Diagnostische und Therap. Verfahren, Z. Kardio 89:239-244 (2000), Feb. 15, 2000.

Wulf D. Ito, et al, "Monocyte Chemotactic Protein-1 Increases Collateral and Peripheral Conductance After Femoral Artery Occlusion," Max-Planck-Institute for Physiological and Clinical Researach, Bad Nauheim, Germany, Feb. 21, 1997, pp. 829-837.

Mia Kalltorp, et al., "Inflammatory Cell Recruitment, Distribution, and Chemiluminescence Response at IgG Precoated- and Thiol Functionalized Gold Surfaces," Swedish Biomaterials Consortium, Swedish Foundation for Strategic Research, Apr. 9, 1999, pp. 251-259.

Nicholas Kipshidze, MD. PhD, et al., "Therapeutic Angeiogenesis for Critical Limb Ischemia to Limit or Avoid Amputation," Medical College of Wisconsin, University of Wisconsin Medical School, The Journal of Invasive Cardiology, vol. 11, No. 1, Jan. 1999, pp. 25-28.

Bruce D. Klugherz, et al., "Gene Delivery From a DNA COIntrolled-Release Stent in Porcine Coronary Arteries," Nature Biotechnology, vol. 18, Nov. 2000, pp. 1181-1184.

K. Kohilas, et al., "Effects of Prosthetic Titanium Wear Debris on Mitogen-Induced Monocyte and Lymphoid Activation," Johns Hopkins University, Dept. of Orthopaedic Surgery, Apr. 1999, pp. 95-103.

S. Joseph Leibovich, et al., "Macrophage-Induced Angiogenesis Is Mediated By Tumour Necrosis Factor-α," Depts. of Oral Biology and Pathology, Northwestern University Dental School, Nature vol. 329, Oct. 15, 1997, pp. 630-633.

John J. Lopez, et al., "Angiogenic Potential of Perivascularly Delivered aFGF in a Porcine Model of Chronic Myocardial Ischemia," The American Physiological Society, 0363-6135/98, 1998, pp. H930-H936.

Serjan D. Nikolic, et al., "Novel Means to Improve Coronary Blood Flow," Clinical Science, Abstracts From Scientific Sessions 2000, p. II-689.

Michael Simons, MD, et al., "Clinical Trials in Coronary Angiogenesis: Issues, Problems, Consensus, an Expert Panel Summary," Angiogenesis Research Center, American Heart Association, Inc., Circulation, Sep. 12, 2000, pp. 1-14.

G. Spenlehauer, et al., "In Vitro and In Vivo Degradation of Poly (D, L Lactide/Glycolide) Type Microspheres Made by Solvent Evaporation Method," Biomaterials, Oct. 1989, vol. 10, pp. 557-563.

Willem J. ven der Giessen, MD, et al., "Marked Inflammatory Sequelae to Implantation of Biodegradable and Nonbiodegradable Polymers in Porcine Coronary Arteries," Dept. of Cardiology, Erasmus University Rotterdam, Circulation, vol. 94, No. 7, Oct. 1, 1996, pp. 1690-1697.

G. E. Visscher, M.A., et al., "Tissue Response to Biodegradable Injectable Microcapsules," Journal of Biomaterials Applications, vol. 2, Jul. 1987, pp. 118-119.

Kawai, Katsuya, et al., "Accelerated Tissue Regeneration Through Incorporation of Basic Fibroblast Growth Factor-Impregnated Gelatin Microspheres into Artificial Dermis", *Biomaterials 21*, (2000),489-499.

Rowley, Jon A., et al., "Alginate Hydrogels as Synthetic Extracellular Matrix Materials", *Biomaterials 20*, (1999),45-53.

Abbott Cardiovascular Systems Inc., PCT Search Report and Written Opinion dated Aug. 26, 2008 for PCT/US2007/016433.

Abbott Cardiovascular Systems in, PCT Search Report and Written Opinion dated Jul. 31, 2008 for PCT/US2007/024158.

Abbott Cardiovascular Systems in, "PCT Search Report dated Feb. 12, 2008", PCT Appln No. PCT/US2007/013181, 17.

Abbott Cardiovascular Systems in, "PCT Search Report dated Jan. 31, 2007", PCT Appln No. PCT/US2006/014021, 11.

Abbott Cardiovascular Systems in, "PCT Search Report dated Mar. 27, 2008", PCT Appln No. PCT/US2007/003614, 18.

Advanced Cardiovascular Systems, Inc., et al., "PCT International Preliminary Report on Patentability dated Jun. 19, 2007", PCT Appln. No. PCT/US2005/045627.

Advanced Cardiovascular Systems, Inc., "PCT International Preliminary Report on Patentability dated Nov. 3, 2005", PCT Appln. No. PCT/US2004/011356, 6 pages.

Advanced Cardiovascular Systems, Inc., "PCT International Search Report and Written Opinion mailed Oct. 13, 2006", PCT Appln No. PCT/US2005/045627.

Advanced Cardiovascular Systems, Inc., "PCT International Search Report dated Feb. 9, 2004", PCT Appln. No. PCT/US03/30464, 5 pages.

Advanced Cardiovascular Systems, Inc., "PCT International Search Report dated Jan. 28, 2004", PCT Appln. No. PCT/US03/18360, 7 pages.

Advanced Cardiovascular Systems, Inc., "PCT Invitation to Pay Additional Fees mailed Nov. 4, 2003", PCT Appln No. PCT/US03/18360, 3 pages.

Advanced Cardiovascular Systems, Inc., "PCT Search Report and Written Opinion dated Nov. 24, 2004", PCT Appln. No. PCT/US2004/011356, 12 pages.

Agocha, A., et al., "Hypoxia regulates basal and induced DNA synthesis and collagen type I production in human cardiac fibroblasts: effects of transforming growth factor-beta 1, thyroid hormone, angiotensin II and basic fibroblast growth factor", J. Mol. Cell. Cardiol., 29(8), (Apr. 1997), pp. 2233-2244.

Allemann, E., et al., "Kinetics of Blood Component Adsorption on poly(D,L-lactic acid) Nanoparticles: Evidence of Complement C3 Component Involvement", J. Biomed. Mater. Res., 37(2), Abstract downloaded from the Internet at: http://www.ncbi.nlm.nih.gov/entrez/query.fcgi?cmd=Retrieve&db=PubMed, (Nov. 1997), pp. 229-234.

Assmus, B., et al., "Transplantation of Progenitor Cells and Regeneration Enhancement in Acute Myocardial Infarction (TOPCARE-AMI)", Circulation, 106, (2002), 3009-3017, first page only.

Baxter, "FloSeal Matrix Hemostatic Sealant", downloaded from the Internet on Nov. 14, 2002, from: http://www.fusionmed.com/docs/surgeon/default.asp, 2 pages.

Berger, et al., "Poly-L-cysteine", J. Am. Chem. Soc., 78(17), (Sep. 5, 1956), pp. 4483-4488.

Bernatowicz, M., et al., "Preparation of Boc-[S-(3-nitro-2-pyridinesulfenyl)]-cysteine and its use for Unsymmetrical Disulfide Bond Formation", Int. J. Peptide Protein Res. 28(2), (Aug. 1996), pp. 107-112.

Boland, E. D., "Electrospinning Collagen and Elastin: Preliminary Vascular Tissue Engineering", Frontiers in Bioscience, vol. 9, (May 1, 2004), pp. 1422-1432.

Brust, G., "Polyimides", downloaded from the Internet at: http://www.pslc.ws/macrog/imide.htm, (2005), 4 pages.

Canderm Pharma, "Technical Dossier: Artecoll", downloaded from the Internet on Oct. 22, 2002 from: http://www.canderm.com/artecoll/tech.html, 3 pages.

Capan, Y., et al., "Preparation and Characterization of Poly(D,L-lactide-co-glycolide) Microspheres for Controlled Release of Human Growth Hormone", AAPS PharmSciTech.; 4(2): article 28, Downloaded from the Internet at: http://www.aapspharmscitech.org/view.asp?art=pt040228&pdf=yes, (2003), 12 pages.

Carpino, L., et al., "Tris(2-aminoethyl)amine as a Substitute for 4-(Aminomethyl)piperidine in the FMOC/Polyamine Approach to Rapid Peptide Synthesis", J. Org. Chem., 55(5), (Mar. 1990), pp. 1673-1675.

Chandy, et al., "The development of porous alginate/elastin/PEG composite matrix for cardiovascular engineering", Journal of Biomaterials Applications, vol. 17, (Apr. 2003), 287-301.

Choi, Young Seon, et al., "Study on gelatin-containing artificial skin: I. Preparation and characteristics of novel gelatin-alginate sponge", Biomaterials, vol. 20, (1999), 409-417.

Corbett, S., et al., "Covalent Cross-linking of Fibronectin to Fibrin is Required for Maximal Cell Adhesion to a Fibronectin-Fibrin Matrix", The Journal of Biological Chemistry, 272(40), (Oct. 3, 1997), pp. 24999-25005.

Creemers, E., et al., "Matrix Metalloproteinase Inhibition After Myocardial Infarction: A New Approach to Prevent Heart Failure?", Circ. Res., vol. 89, (2001), pp. 201-210.

Crivello, et al., "Synthesis and Photoinitiated Cationic Polymerization of Monomers with the Silsesquioxane Core", J Polym Science: Part A: Polymer Chemistry 35, (1997), pp. 407-425.

Davis, M. E., et al., "Injectable Self-Assembling Peptide Nanofibers Create Intramyocardial Microenvironments for Endothelial Cells", Circulation, 111, (Feb. 2005), pp. 442-450.

De Rosa, et al., "Biodegradable Microparticles for the Controlled Delivery of Oligonucleotides", International Journal of Pharmaceutics, 242, (Aug. 21, 2002), pp. 225-228.

Desai, M., et al., "Polymer bound EDC (P-EDC): A convenient reagent for formation of an amide bond", Tetrahedron Letters, 34(48), Abstract downloaded from the Internet at: http://www.sciencedirect.com, 1 page, (Nov. 1993), pp. 7685-7688.

Dinbergs, et al., "Cellular response to transforming growth factor-β1 and basic fibroblast growth factor depends on release kinetics and extracellular matrix interactions", The Journal of Biological Chemistry, vol. 271, No. 47, (Nov. 1996), 29822-29829.

Dong, Zhanfeng, et al., "Alginate/gelatin blend films and their properties for drug controlled release", Journal of Membrane Science, vol. 280, (2006), 37-44.

Edelman, "Controlled and modulated release of basic fibroblast growth factor", Biomaterials, vol. 12, (Sep. 1999), 619-626.

Etzion, S., et al., "Influence of Embryonic Cardiomyocyte Transplantation on the Progression of Heart Failure in a Rat Model of Extensive Myocardial Infarction", J. Mol. Cell Cardiol., 33, (May 2001), pp. 1321-1330.

Ferrara, N., "Role of Vascular Endothelial Growth Factor in the Regulation of Angiogenesis", Kidney International, 56(3), Abstract downloaded from the Internet at: http://www.nature.com/ki/journal/v56/n3/abs/4490967a.html, 1 page, (1999), pp. 794-814.

Fuchs, S., et al., "Catheter-Based Autologous Bone Marrow Myocardial Injection in No-Option Patients with Advanced Coronary Artery Disease", J. Am. Coll. Cardiol., 41(10), (2003), pp. 1721-1724.

Fukumoto, S., et al., "Protein Kinase C δ Inhibits the Proliferation of Vascular Smooth Muscle Cells by Suppressing G1 Cyclin Expression", The Journal of Biological Chemistry, 272(21), (May 1997), pp. 13816-13822.

Giordano, F., et al., "Angiogenesis: The Role of the Microenvironment in Flipping the Switch", Current Opinion in Genetics and Development, 11, (2001), pp. 35-40.

Gossler, et al., "Transgenesis by means of blastocyst-derived embryonic stem cell lines", Proc. Natl. Acad. Sci. USA, 83, (Dec. 1986), pp. 9065-9069.

Grafe, T. H., "Nanofiber Webs from Electrospinning", Presented at the Nonwovens in Filtration—Fifth International Conference, Stuttgart, Germany, (Mar. 2003), pp. 1-5.

Gref, R., et al., "Biodegradable Long-Circulating Polymeric Nanospheres", Science, 263(5153), Abstract downloaded from the Internet at: http://www.sciencemag.org/cgi/content/abstract/263/5153/1600, 1 page, (Mar. 1994), pp. 1600-1603.

Grund, F., et al., "Microembolization in Pigs: Effects on Coronary Blood Flow and Myocardial Ischemic Tolerance", Am. J. Physiol., 277 (Heart Circ. Physiol. 46), (1999), pp. H533-H542.

Gupta, et al., "Changes in Passive Mechanical Stiffness of Myocardial Tissue with Aneurysm Formation", Circulation, 89(5), (May 1994), pp. 2315-2326.

Hanawa, T., et al., "New oral dosage form for elderly patients: preparation and characterization of silk fibroin gel", Chemical and Pharmaceutical Bulletin, Pharmaceutical Society of Japan, Tokyo, vol. 43, No. 2, (Jan. 1995), 284-288.

Hashimoto, T., et al., "Development of Alginate Wound Dressings Linked with Hybrid Peptides Derived from Laminin and Elastin", Biomaterials, 25, (2004), pp. 1407-1414.

Haugland, et al., "Dialkylcarbocyanine and Dialkylaminostryryl Probes", Handbook of Fluorescent Probes and Research Products, Molecular Probes, Inc., (2002), 530-534.

Haugland, et al., "Membrane-permeant reactive tracers", Handbook of Fluorescent Probes and Research Products, Molecular Probes, Inc., (2002), 458-553.

Heeschen, C., et al., "Nicotine Stimulates Tumor Angiogenesis", American College of Cardiology, 37(2) Supplement A,, Abstract downloaded from the Internet at: http://24.132.160.238/ciw-01acc/abstract_search_author.cfm?SearchName=Heeschen, 1 page, (Feb. 2001), pp. 1A-648A.

Hendel, R. C., et al., "Effect of Intracoronary Recombinant Human Vascular Endothelial Growth Factor on Myocardial Perfusion: Evidence for a Dose-Dependent Effect", Circulation, 101, (2000), pp. 118-121.

Henry, R. R., et al., "Insulin Action and Glucose Metabolism in Nondiabetic Control and NIDDM Subjects: Comparison Using Human Skeletal Muscle Cell Cultures", Diabetes, 44(8), Abstract downloaded from the Internet at: http://diabetes.diabetesjournals.org/cgi/content/abstract/44/8/936, 1 page, (1995), pp. 936-946.

Hoffman, "Hydrogels for Biomedical Applications", Advanced Drug Delivery Reviews, vol. 43, (2002), pp. 3-12.

Holland, N. B., et al., "Biomimetic Engineering of Non-Adhesive glycocalyx-like Surfaces Using Oligosaccharide Surfactant Polymers", Nature, 392, Abstract downloaded from the Internet at: http://www.nature.com, 1 page, (Apr. 1998), pp. 799-801.

Horan, R.L., et al., "In Vitro Degradation of Silk Fibroin", Biomaterials, vol. 26, (2004), 3385-3393.

Hovinen, J., et al., "Synthesis of 3'-functionalized oligonucleotides on a single solid support", Tetrahedron Letters, 34(50), Abstract downloaded from the Internet at: http://www.sciencedirect.com, 1 page, (Dec. 1993), pp. 8169-8172.

Huang, K., et al., "Synthesis and Characterization of Self-Assembling Block Copolymers Containing Bioadhesive End Groups", Biomacromolecules, 3(2), (2002), pp. 397-406.

Hutcheson, K., et al., "Comparison of Benefits on Myocardial Performance of Cellular Cardiomyoplasty with Skeletal Myoblasts and Fibroblasts", Cell Transplantation, 9(3), (2000), pp. 359-368.

Huynh, T. V., et al., "Constructing and Screening cDNA Libraries in λgt10 and λgt11", Chapter 2 in DNA Cloning, vol. 1: A Practical Approach, ed. by D.M. Glover, (1985), pp. 49-78.

Indik, Z., et al., "Production of Recombinant Human Tropoelastin: Characterization and Demonstration of Immunologic and Chemotactic Activity", Arch. Biochem. Biophys., 280(1), Abstract downloaded from the Internet at: http://www.ncbi.nlm.nih.gov/entrez/query.fcgi?cmd=Retrieve&db=PubMed, 1 page, (Jul. 1990), pp. 80-86.

Iskandrian, A. S., et al., "Nuclear Cardiac Imaging: Principles and Applications", second edition, F.A. Davis Co., Philadelphia, cover page, title page and TOC, (1996), 5 pages total.

Isner, J. M., "Vascular Endothelial Growth Factor: Gene Therapy and Therapeutic Angiogenesis", Am. J. Cardiol., 82(10A), (Nov. 19, 1998), pp. 63S-64S.

Johnson, et al., "The stabilization and encapsulation of human growth hormone nto biodegradable microspheres", Pharmaceutical Research, vol. 14, No. 6, (1997), 730-735.

Jonasson, P. , et al., "Denatured states of human carbonic anhydrase II: an NMR study of hydrogen/deuterium exchange at tryptophanindole-Hn sites", FEBS Letters, 445, (1999), pp. 361-365.

Kaplan, D.L., et al., "Spiderless Spider Webs", Nature Biotechnology, vol. 20, (2002), 239-240.

Kawasuji, M., et al., "Therapeutic Angiogenesis with Intramyocardial Administration of Basic Fibroblast Growth Factor", Ann Thorac Surg, 69, Abstract downloaded from the Internet at: http://ats.ctsnetjournals.org/cgi/content/abstract/69/4/1155, 2 pages, (2000), pp. 1155-1161.

Kelley, et al., "Restraining Infarct Expansion Preserves Left Ventricular Geometry and Function After Acute Anteroapical Infarction", Circulation, 99, (1999), pp. 135-142.

Kelly, E. B., "Advances in Mammalian and Stem Cell Cloning", Genetic Engineering News, vol. 23, No. 7, (Apr. 1, 2003), pp. 17-18 & 68.

Khademhosseini, et al., "Microscale Technologies for Tissue Engineering and Biology", PNAS, vol. 103, No. 8, (Feb. 21, 2006), pp. 2480-2487.

Kim, D., et al., "Glow Discharge Plasma Deposition (GDPD) Technique for the Local Controlled Delivery of Hirudin from Biomaterials", Pharmaceutical Research, 15(5), (1998), pp. 783-786.

Kim, Ung-Jin, et al., "Structure and Properties of Silk Hydrogels", Biomacromolecules, vol. 5(3), (2004), 786-792.

Kinart, et al., "Electrochemical Studies of 2-hydroxy-3-(3,4-dimethyl-9-oxo-9H-thioxanthen-2-yloxy)N,N,N-trimethyl-1-propanium chloride", J. Electroanal. Chem, 294, (1990), pp. 293-297.

Klein, S., et al., "Fibroblast Growth Factors as Angiogenesis Factors: New Insights Into Their Mechanism of Action", Regulation of Angiogenesis, I.D. Goldberg and E.M. Rosen (eds.), 79, (1997), pp. 159-192.

Kweon, H. Y., et al., "Preparation of semi-interpenetrating polymer networks composed of silk fibroin and poly(ethyleneglycol) macromer", Journal of Applied Polymer Science, John Wiley and Sons Inc., New York, NY, vol. 80, (Jan. 2001), 1848-1853.

Kwok, C., et al., "Design of Infection-Resistant Antibiotic-Releasing Polymers: I. Fabrication and Formulation", Journal of Controlled Release, 62, (1999), pp. 289-299.

Laboratory of Liposome Research, "Liposomes: General Properties", downloaded from the Internet on Feb. 9, 2006 at: http://www.unizh.ch/onkwww/lipos.htm, 5 pages.

Laham, R. J., "Intrapericardial Delivery of Fibroblast Growth Factor-2 Induces Neovascularization in a Porcine Model of Chronic Myocardial Ischemia", J. Pharmacol Exper Therap, 292(2), (2000), pp. 795-802.

Leor, J., et al., "Bioengineered Cardiac Grafts—A New Approach to Repair the Infarcted Myocardium?", Circulation, 102[suppl III], (2000), pp. III-56-III-61.

Leor, J., et al., "Gene Transfer and Cell Transplant: An Experimental Approach to Repair a 'Broken Heart'", Cardiovascular Research, 35, (1997), pp. 431-441.

Leroux, J. C., et al., "An Investigation on the Role of Plasma and Serum Opsonins on the Internalization of Biodegradable poly(D,L-lactic acid) Nanoparticles by Human Monocytes", Life Sci., 57(7), Abstract downloaded from the Internet at: http://www.ncbi.nlm.nih.gov/entrez/query.fcgi?cmd=Retrieve&db=pubmed, 1 page, (1995), pp. 695-703.

Lewin, B., "Repressor is Controlled by a Small Molecule Inducer", Genes VII, Oxford University Press, 7th ed., (2000), pp. 277-280.

Li, et al., "Cell Therapy to Repair Broken Hearts", Can. J. Cardiol., vol. 14, No. 5, (May 1998), pp. 735-744.

Li, W. W., et al., "Lessons to be Learned from Clinical Trials of Angiogenesis Modulators in Ischemic Diseases", Angiogenesis in Health & Disease: Basic Mechanisms and Clinical Applications, Rubanyi, G. (ed), Marcel Dekker, Inc. New York, (2000), Chapter 33.

Li, J., et al., "PR39, A Peptide Regulator of Angiogenesis", Nature Medicine, 6(1), (Jan. 2000), pp. 49-55.

Li., Y. Y., et al., "Differential Expression of Tissue Inhibitors of Metalloproteinases in the Failing Human Heart", Circulation, 98(17), (1998), pp. 1728-1734.

Lindsey, M., et al., "Selective Matrix Metalloproteinase Inhibition Reduces Left Ventricular Remodeling but does not Inhibit Angiogenesis after Myocardial Infarction", Circulation, 105(6), (2002), pp. 753-758.

Long, D. M., et al., "Self-Cleaving Catalytic RNA", FASEB Journal, 7, (1993), pp. 25-30.

Lopez, J. J., et al., "VEGF Administration in Chronic Myocardial Ischemia in Pigs", Cardiovasc. Res., 40(2), Abstract downloaded from the Internet at: http://www.ncbi.nlm.nih.gov/entrez/query.fcgi?cmd=Retrieve&db=pubmed, 1 page, (1998), pp. 272-281.

Lu, L., et al., "Biodegradable Polymer Scaffolds for Cartilage Tissue Engineering", Clinical Orthopaedics and Related Research, Carl T. Brighton (ed.). No. 391S, (2001), pp. S251-S270.

Luo, Y., et al., "Cross-linked Hyaluronic Acid Hydrogel Films: New Biomaterials for Drug Delivery", Journal of Controlled Release, 69, (2000), pp. 169-184.

Lutolf, M, et al., "Synthesis and Physicochemical Characterization of End-Linked Poly(ethylene glycol)-co-peptide Hydrogels Formed by Michael-Type Addition", Biomacromolecules, vol. 4, (2003), 713-722.

Lyman, M. D., et al., "Characterization of the Formation of Interfacially Photopolymerized Thin Hydrogels in Contact with Arterial Tissue", Biomaterials, 17(3), (1996), pp. 359-364.

Mansour, S., et al., "Disruption of the proto-oncogene int-2 in mouse embryo-derived stem cells: a general strategy for targeting mutations to non-selectable genes", Nature, 336, (1988), pp. 348-352.

Martin, S. L., et al., "Total Synthesis and Expression in *Escherichia coli* of a Gene Encoding Human Tropoelastin", Gene, (1995), Abstract, 1 page.

McDevitt, T., et al., "In vitro Generation of Differentiated Cardiac Myofibers on Micropatterned Laminin Surfaces", J. Biomed Mater Res., 60, (2002), pp. 472-479.

Meinel, L., et al., "The Inflammatory Responses to Silk Films In Vitro and In Vivo", Biomaterials, vol. 26, (2005), 147-155.

Narmoneva, D. A., et al., "Self-assembling short oligopeptides and the promotion of angiogenesis", Biomaterials, 26, (2005), pp. 4837-4846.

Nazarov, R., et al., "Porous 3-D Scaffolds from Regenerated Silk Fibroin", Biomacromolecules, vol. 5(3), (2004), 718-726.

Nguyen, K. T., et al., "Photopolymerizable Hydrogels for Tissue Engineering Applications", Biomaterials, 23, (2002), pp. 4307-4314.

Nikolic, S. D., et al., "New Angiogenic Implant Therapy Improves Function of the Ischemic Left Venticle", Supplement to Circulation; Abstracts From Scientific Sessions 2000, 102(18), (Oct. 2000), pp. II-689, Abstract 3331.

Nitinol Technical Information, "NiTi Smart Sheets", downloaded from the Internet on Dec. 10, 2002 at: http://www.sma-inc.com/information.html, 1 page.

Nose, et al., "A novel cadherin cell adhesion molecule: its expression patterns associated with implantation and organogenesis of mouse embryos", Journal of Cell Biology, vol. 103 (No. 6, Pt. 2), The Rockefeller University Press, (Dec. 1986), 2649-2658.

Ohyanagi, H., et al., "Kinetic Studies of Oxygen and Carbon Dioxide Transport into or from Perfluorochemical Particles", Proc. ISAO, vol. 1 (Artificial Organs vol. 2 (Suppl.)), (1977), pp. 90-92.

Ozbas, B., et al., "Salt-Triggered Peptide Folding and Consequent Self-Assembly into Hydrogels with Tunable Modulus", Macromolecules, 37(19), (2004), pp. 7331-7337.

Ozbas-Turan, S., "Controlled Release of Interleukin-2 from Chitosan Microspheres", Journal of Pharmaceutical Sciences, 91(5), (May 2002), pp. 1245-1251.

Palmiter, R., et al., "Germ-Line Transformation of Mice", Ann. Rev. Genet., 20, (1986), pp. 465-499.

Patrick, C. R., "Mixing and Solution Properties of Organofluorine Compounds", Preparation, Properties and Industrial Applications of Organofluorine Compounds, Chapter 10, R.E. Banks (ed.), 1st edition, Ellis-Horwood Ltd., Chichester:England, (1982), pp. 323-342.

Peattie, R. A., et al., "Stimulation of In Vivo Angiogenesis by Cytokine-Loaded Hyaluronic Acid Hydrogel Implants", Biomaterials, 25(14), Abstract downloaded from: www.sciencedirect.com, (Jun. 2004), 2 pages.

Penta, K., et al., "Del1 Induces Integrin Signaling and Angiogenesis by Ligation of α V β 3", J. Biolog. Chem., 274(16), (Apr. 1999), pp. 11101-11109.

Perin, E. C., et al., "Transendocardial, Autologous Bone Marrow Cell Transplantation for Severe, Chronic, Ischemic Heart Failure", Circulation, (2003), 1 page.

Pouzet, B., et al., "Is Skeletal Myoblast Transplantation Clinically Relevant in the Era of Angiotensin-Converting Enzyme Inhibitors?", Circulation, 104 [suppl I], (Sep. 2001), pp. I-223-I-228.

Prather, et al., "Nuclear Transplantation in Early Pig Embryos", Biol. Reprod., 41, (1989), pp. 414-418.

Prosci Incorporated, "ILPIP (CT) Peptide", 1 page.

Quellec, P., et al., "Protein Encapsulation Within Polyethylene Glycol-coated Nanospheres. I. Physicochemical Characterization", J. Biomed. Mater. Res., 42(1), (1998)), Abstract, 1 page.

Ramirez-Solis, R., et al., "Gene Targeting in Embryonic Stem Cells", Methods in Enzymology, 225, (1993), pp. 855-878.

Sawhney, A. S., et al., "Bioerodible Hydrogels Based on Photopolymerized Poly(ethylene glycol)-co-poly(a-hydroxy acid) Diacrylate Macromers", Macromolecules, 26(4), (1993), pp. 581-587.

Sbaa-Ketata, E., et al., "Hyaluronan-Derived Oligosaccharides Enhance SDF-1-Dependent Chemotactic Effect on Peripheral Blood Hematopoietic CD34+ Cells", Stem Cells, 20(6), Letter to the Editor downloaded from the Internet at: http://stemcells.alphamedpress.org/cgi/content/full/20/6/585, (2002), 585-587.

Segura, T, et al., "Crosslinked Hyaluronic Acid Hydrogels: A Strategy to Functionalize and Pattern", Biomaterials, vol. 26(4), (Feb. 2005), 359-371.

Segura, T, et al., "DNA delivery from hyaluronic acid-collagen hydrogels via a substrate-mediated approach", Biomaterials, vol. 26, (2005), 1575-1584.

Segura, T., et al., "Substrate-Mediated DNA Delivery: Role of the Cationic Polymer Structure and Extent of Modification", Journal of Controlled Release, 93, (2003), pp. 69-84.

Segura, T., et al., "Surface-Tethered DNA Complexes for Enhanced Gene Delivery", Bioconjugate Chem, 13(3), (2002), pp. 621-629.

Shibasaki, F., et al., "Suppression of Signalling Through Transcription Factor NF-AT by Interactions Between Calcineurin and Bcl-2", Nature, 386(6626), Abstract downloaded from the Internet at: http://www.ncbi.nlm.nih.gov/entrez/query.fcgi?CMD=Text&DB=pubmed, 1 page, (1997).

Shin, H., et al., "Attachment, Proliferation, and Migration of Marrow Stromal Osteoblasts Cultured on Biomimetic Hydrogels Modified with an Osteopontin-Derived Peptide", Biomaterials, 25, (2004), pp. 895-906.

Shin, H., et al., "In vivo bone and soft tissue response to injectable, biodegradable oligo(poly(ethylene glycol) fumarate) hydrogels", Biomaterials 24, Elseview Science Ltd., (3201-3211), 2003.

Shu, Z., et al., "Disulfide-crosslinked hyaluronan-gelatin hydrogel films: a covalent mimic of the extracellular matrix for in vitro cell growth", Biomaterials, vol. 24(21), (Sep. 2003), 3825-3834.

Shu, Zheng, et al., "In situ crosslinkable hyaluronan hydrogels for tissue engineering", Biomaterials, vol. 25, (2004), 1339-1348.

Spinale, F. G., "Matrix Metalloproteinases—Regulation and Dysregulation in the Failing Heart", Circ. Res., 90, (2002), pp. 520-530.

Springer, M., et al., "Angiogenesis Monitored by Perfusion with a Space-Filling Microbead Suspension", Mol. Ther., 1(1), Abstract downloaded from the Internet at: http://www.ncbi.nlm.nih.gov/entrez/query.fcgi?cmd=Retrieve&db=PubMed, 1 page, (2000), pp. 82-87.

Storm, G., et al., "Surface Modification of Nanoparticles to Oppose Uptake by the Mononuclear Phagocyte System", Advanced Drug Delivery Reviews, 17(1), Abstract downloaded from the Internet at: http://www.sciencedirect.com, 1 page, (Oct. 1995), pp. 31-48.

Strauer, B., et al., "Repair of Infarcted Myocardium by Autologous Intracoronary Mononuclear Bone Marrow Cell Transplantation in Humans", Circulation, 106, (2002), pp. 1913-1918.

Tybulewicz, V., et al., "Neonatal lethality and lymphopenia in mice with a homozygous disruption of the c-abl proto-oncogene", Cell, 65(7), Abstract downloaded from the Internet at: http://www.sciencedirect.com, 2 pages, (Jun. 1991), pp. 1153-1163.

Unger, E. F., et al., "Effects of a Single Intracoronary Injection of Basic Fibroblast Growth Factor in Stable angina Pectoris", Am. J. Cardiol, 85(12), Abstract downloaded from the Internet at: http://www.sciencedirect.com, 2 pages, (Jun. 2000), pp. 1414-1419.

Van Luyn, M. J., et al., "Cardiac Tissue Engineering: Characteristics of in Unison Contracting Two- and Three-Dimensional Neonatal Rat Ventricle Cell (Co)-Cultures", Biomaterials, 23, (2002), pp. 4793-4801.

Vercruysse, K. P., et al., "Synthesis and in Vitro Degradation of New Polyvalent Hydrazide Cross-Linked Hydrogels of Hyaluronic Acid", Bioconjugate Chem, 8(5), Abstract downloaded from the Internet at: http://pubs.acs.org/cgi-bin/abstract.cgi/bcches/1997/8/i05/abs/bc9701095.html, 1 page, (1997), pp. 686-694.

Vlodavsky, I., et al., "Extracellular Matrix-resident Basic Fibroblast Growth Factor: Implication for the Control of Angiogenesis", J. Cell Biochem, 45(2), Abstract downloaded from the Internet at: http://www.ncbi.nlm.nih.gov/entrez/query.fcgi?cmd=Retrieve&db=PubMed, 1 page, (Feb. 1991), pp. 167-176.

Wang, M., et al., "Mechanical Properties of Electrospun Silk Fibers", Macromolecules, vol. 37(18), (2004), 6856-6864.

Wasielewski, "Ischamische Erkrankungen, Gefassneubildung anregen", Deutsche Apotheker Zeitung, vol. 140, No. 3, Stuttgart (DE), (Jan. 20, 2000), 232-233.

Wilensky, R., et al., "Direct intraarterial wall injection of microparticles via a catheter: a potential durg delivery strategy following angioplasty", American Heart Journal, 122, (1991), p. 1136.

Witzenbichler, B., et al., "Vascular Endothelial Growth Factor-C (VEGF-C/VEGF-2) Promotes Angiogenesis in the Setting of Tissue Ischemia", Am Pathol., 153(2), (Aug. 1998), pp. 381-394.

Yager, P., et al., "Silk Protein Project", www.faculty.washington.edu/yagerp/silkprojecthome.html, (Aug. 23, 1997), 18 pages.

Yamamoto, N., et al., "Histologic evidence that basic fibroblast growth factor enhances the angiogenic effects of transmyocardial laser revascularization", Basic Research in Cardiology, vol. 95, No. 1, (Feb. 1, 2000), 55-63.

Yeo, L.Y., et al., "AC Electrospray Biomaterials Synthesis", Biomaterials, (2005), 7 pages.

Zervas, L., et al., "On Cysteine and Cystine Peptides. II. S-Acylcysteines in Peptide Synthesis", J. Am. Chem. Soc., 85(9), (May 1963), pp. 1337-1341.

Zheng, W., et al., "Mechanisms of coronary angiogenesis in response to stretch: role of VEGF and TGF-beta", Am J Physiol Heart Circ Physiol., 280(2), (Feb. 2001), pp. H909-H917.

Zimmermann, W., et al., "Engineered Heart Tissue for Regeneration of Diseased Hearts", Biomaterials, 25, (2004), pp. 1639-1647.

Abbott Cardiovascular Systems Inc., PCT International Preliminary Report on Patentability and Written Opinion dated Dec. 24, 2008 for PCT/US2007/013181, 11 pages.

Abbott Cardiovascular Systems Inc, PCT International Search Report and Written Opinion mailed Feb. 10, 2009 for PCT Application No. PCT/US2007/023419, 17 pages.

Friedman, Paul M. et al., "Safety Data of Injectable Nonanimal Stabilized Hyaluronic Acid Gel for Soft Tissue Augmentation," Dermatologic Surgery, 2002, vol. 28, pp. 491-494.

Abbott Cardiovascular Systems, Office Action mailed Apr. 6, 2009 for U.S. Appl. No. 11/447,340.

Abbott Cardiovascular Systems, Office Action mailed Mar. 30, 2009 for U.S. Appl. No. 10/792,960.

Abbott Cardiovascular Systems, Office Action mailed Apr. 13, 2009 for U.S. Appl. No. 11/566,643.

Elbert, D. L., et al., "Protein delivery from materials formed by self-selective conjugate addition reactions", Journal of Controlled Release, 76, (2001), 11-25.

Abbott Cardiovascular Systems, Non Final Office Action dated May 12, 2009 for U.S. Appl. No. 11/496,824.

Abbott Cardiovascular Systems, Non Final Office Action dated Mar. 13, 2009 for U.S. Appl. No. 10/414,602.

Abbott Cardiovascular Systems, International search report and written opinion dated Jun. 18, 2009 for PCT/US2008/051505.

Abbott Cardiovascular Systems, Non final office action dated Jul. 9, 2009 for U.S. Appl. No. 11/561,328.

Abbott Cardiovascular Systems, Non final Office Action dated Apr. 29, 2009 for U.S. Appl. No. 12/013,286.

Staatz, WD, et al., "Identification of a tetrapeptide recognition sequence for the alpha 2 beta 1 integrin in collagen", Journal of Biological Chemistry, 1991, 266(12), pp. 7363-7367.

Abbott Cardiovascular Systems, International Preliminary Report on Patentability dated Jul. 30, 2009 for PCT/US2008/051505.

Abbott Cardiovascular Systems, Final office action dated Nov. 12, 2009 for U.S. Appl. No. 12/013,286.

Abbott Cardiovascular Systems, Final office action dated Nov. 25, 2009 for U.S. Appl. No. 11/566,643.

Abbott Cardiovascular Systems, Examination Report dated Jan. 13, 2010 for EP Application No. 07795729.8.

Abbott Cardiovascular Systems, Non final office action dated Feb. 5, 2010 for U.S. Appl. No. 11/447,340.

Abbott Cardiovascular Systems, Final Office Action dated Jan. 29, 2010 for U.S. Appl. No. 10/792,960.

Shu, Zheng, et al., "In situ crosslinkable hyaluronan hydrogels for tissue engineering", Biomaterials, Elsevier Science Publishers, vol. 25, No. 7-8, (2004), 1339-1348.

Abbott Cardiovascular Systems, Non final office action dated Aug. 13, 2010 for U.S. Appl. No. 11/447,340.

Abbott Cardiovascular Systems, Examination Report dated Jan. 15, 2010 for EP 08727952.7.

Abbott Cardiovascular Systems, Examination Report dated Feb. 5, 2010 for EP 07810637.4.

Abbott Cardiovascular Systems, Non final office action dated Apr. 14, 2010 for U.S. Appl. No. 12/016,180.

Abbott Cardiovascular Systems, Final office action dated Apr. 22, 2010 for U.S. Appl. No. 10/414,602.

Abbott Cardiovascular Systems, Non final office action dated Apr. 29, 2010 for U.S. Appl. No. 10/792,960.

Abbott Cardiovascular Systems, Final Office Action dated Jun. 11, 2010 for U.S. Appl. No. 11/561,328.

Hao, X, et al., "Angiogenic effects of sequential release of VEGF-A165 and PDGF-BB with alginate hydrogels after myocardial infarction", Cardiovascular Research, 75, (2007), 178-185.

Ritter, A. B., et al., "Elastic modulus, distensibility, and compliance (capacitance)", Biomedical Engineering Principles, Chapter 4, (2005), 187-191.

Abbott Cardiovascular Systems, Final office action mailed Sep. 27, 2010 for U.S. Appl. No. 10/792,960.

Abbott Cardiovascular Systems, Final office action mailed Sep. 27, 2010 for U.S. Appl. No. 12/016,180.

Abbott Cardiovascular Systems, Non-final Office Action mailed Nov. 24, 2010 for U.S. Appl. No. 12/013,286, 11 pages.

Abbott Cardiovascular Systems, Non-final Office Action mailed Dec. 8, 2010 for U.S. Appl. No. 11/566,643., 17 pages.

Abbott Cardiovascular Systems, Non-final Office Action mailed Dec. 10, 2010 for U.S. Appl. No. 11/938,752., 32 pages.

Abbott Cardiovascular Systems, Non-final Office Action mailed Dec. 17, 2010 for U.S. Appl. No. 11/933,922, 23 pages.

Abbott Cardiovascular Systems, website for HEALON (R) OVD, copyright 2010, accessed Dec. 15, 2010, URL: <http://abbottmedicaloptics.com/products/cataract/ovds/healon-viscoelastic>, (2010), 2 pages.

Abbott Cardiovascular Systems, Product Information Sheet for HEALON (R), from Abbott Medical Optics, (2005), 1 page.

Abbott Cardiovascular Systems, Japanese Office Action dated Dec. 8, 2010 for Japanese Patent App No. 2006-509975., 6 pages.

Haynesworth, Stephen E., et al., "Platelet Effects on Human Mesenchymal Stem Cells", Abstract, presented at Orthopaedic Research Society 48th Annual Meeting, Dallas, TX, (Feb. 10-13, 2010), 2 pages.

Abbott Cardiovascular Systems, Non final office action mailed Feb. 8, 2011 for U.S. Appl. No. 10/792,960.

Abbott Cardiovascular Systems, Final Office Action mailed Apr. 15, 2011 for U.S. Appl. No. 10/414,602.

Abbott Cardiovascular Systems, Non final office action mailed Jun. 7, 2011 for U.S. Appl. No. 11/447,340.

Advanced Cardiovascular Systems, Extended European search report dated Apr. 21, 2011 for EP Application No. 10186186.2.

Advanced Cardiovascular Systems, Extended EP Search Report dated May 20, 2011 for EP Application No. 10186197.9.

Chung, Y. , et al., "Sol-gel transition temperature of PLGA-g-PEG aqueous solutions", Biomacromolecules, vol. 3, No. 3, (May 2002), 511-516.

Abbott Cardiovascular Systems, Final office action mailed Jun. 28, 2011 for U.S. Appl. No. 10/792,960.

Abbott Cardiovascular Systems, Final office action mailed Jul. 18, 2011 for U.S. Appl. No. 11/566,643.

Abbott Cardiovascular Systems, Non-Final Office Action mailed Aug. 31, 2011 for U.S. Appl. No. 11/110,223.

Abbott Cardiovascular Systems, Final office action mailed Sep. 20, 2011 for U.S. Appl. No. 11/938,752.

Abbott Cardiovascular Systems, Non final office action mailed Nov. 8, 2011 for U.S. Appl. No. 10/792,960.

Abbott Cardiovascular Systems, Final Office Action mailed Jan. 5, 2012 for U.S. Appl. No. 11/361,920.

Abbott Cardiovascular Systems, Final Office Action mailed May 9, 2012 for U.S. Appl. No. 11/110,223.

Abbott Cardiovascular Systems, European Search report for application No. 12151788.2 mailed Apr. 18, 2012, 6 pages.

Abbott Cardiovascular Systems, Non-final Office Action mailed Jun. 26, 2012 for U.S. Appl. No. 12/632,612.

Abbott Cardiovascular Systems, Japanese Office Action dated Jun. 11, 2012 for Appln. No. 2010-162711.

Abbott Cardiovascular Systems, Office Action mailed Jan. 17, 2012 for European Patent Application 08727952.7, 6 pages.

Abbott Cardiovascular Systems, Final Office Action mailed Feb. 8, 2012 for Japanese application No. 2006-509975, 6 pages.

Abbott Cardiovascular Systems, Non-Final Office Action mailed Feb. 15, 2012 for U.S. Appl. No. 12/114,717, 16 pages.

Abbott Cardiovascular Systems, Final Office Action mailed Apr. 4, 2012 for U.S. Appl. No. 10/792,960, 13 pages.

Abbott Cardiovascular Systems, European Office Action mailed Apr. 11, 2012 for App No. 12155231.9, 9 pages.

Abbott Cardiovascular Systems, European Office Action mailed Apr. 10, 2012 for App No. 07810637.4, 6 pages.

Abbott Cardiovascular Systems, Non-Final Office Action Sep. 11, 2012 for U.S. Appl. No. 10/792,960.

Abbott Cardiovascular Systems, et al., Japanese Office Action dated Aug. 27, 2012 for JP 2009-522776.

Abbott Cardiovascular Systems, Non-Final Office Action dated Oct. 3, 2012 for U.S. Appl. No. 12/756,119.

Abbott Cardiovascular Systems, Japanese office action dated Aug. 20, 2012 for JP 2009-537153.

C, Mogan , et al., "Rationale of platelet gel to augment adaptive remodeling of the injured heart", J Extra Corpor Technol, 36(2), (Jun. 2004), 191-196.

Davis, Michael E., et al., "Injectable Self-Assembling Peptide Nanofibers Create Intramyocardial Microenvironments for Endothelial Cells", Circulation, 111, (2005), 442-450.

Hao, Xiaojin , et al., "Angiogenic Effects of Sequential release of VEGF-A 165 and PDGF-BB with Alginate Hydrogels After Myocardial Infarction", Cardiovascular Research, 75(1), (Apr. 6, 2007), 178-185.

\* cited by examiner

AGENTS THAT STIMULATE THERAPEUTIC ANGIOGENESIS AND TECHNIQUES AND DEVICES THAT ENABLE THEIR DELIVERY

This application is a divisional application of U.S. patent application No. 10/011,071, filed Nov. 30, 2001, now U.S. Pat. No. 6,702,744. This application also claims the benefit of the earlier filing date of Provisional Application Ser. No. 60/300,042, filed Jun. 20, 2001, by Evgenia Mandrusov, Murthy V. Simhambhatla, Syed Hossainy, Gene Michal, Chuck Claude, and Jessica G. Chiu, titled "Angiogenesis/Arteriogenesis Treatment Agents and Technique and Device for Locating Treatment Agents," all incorporated herein by reference.

BACKGROUND

1. Field

This invention relates to resolving ischemia by inducing formation of blood vessels through therapeutic angiogenesis.

2. Relevant Art

A major component of morbidity and mortality attributable to cardiovascular disease occurs as a consequence of the partial or complete blockage of vessels carrying blood in the coronary and/or peripheral vasculature. When such vessels are partially occluded, lack of blood flow causes ischemia to the muscle tissues supplied by such vessel, consequently inhibiting muscle contraction and proper function. Total occlusion of blood flow causes necrosis of the muscle tissue.

Blood vessel occlusions are commonly treated by mechanically enhancing blood flow in the affected vessels. Such mechanical enhancements are often provided by employing surgical techniques that attach natural or synthetic conduits proximal and distal to the areas of occlusion, thereby providing bypass grafts, or revascularization by various means to physically enlarge the vascular lumen at the site of occlusion. These revascularization procedures involve such devices as balloons, endovascular knives (atherectomy), and endovascular drills. The surgical approach is accompanied by significant morbidity and even mortality, while the angioplasty-type processes are complicated by recurrent stenoses in many cases.

In some individuals, blood vessel occlusion is partially compensated by natural processes, in which new vessels are formed (termed "angiogenesis") and small vessels are enlarged (termed "arteriogenesis") to replace the function of the impaired vessels. These new conduits may facilitate restoration of blood flow to the deprived tissue, thereby constituting "natural bypasses" around the occluded vessels. However, some individuals are unable to generate sufficient collateral vessels to adequately compensate for the diminished blood flow caused by cardiovascular disease. Accordingly, it would be desirable to provide a method and apparatus for delivering agents to help stimulate the natural process of therapeutic angiogenesis to compensate for blood loss due to an occlusion in a coronary and peripheral arteries in order to treat ischemia.

SUMMARY

A method is disclosed. In one embodiment the method includes positioning a delivery device such as a catheter at a location in a blood vessel and advancing the delivery device a distance into a wall of the blood vessel to a treatment site. A treatment agent is then introduced through the delivery device to the treatment site. The method also includes identifying a treatment site based on imaging a thickness of a portion of the wall of the blood vessel. In the example of introducing a treatment agent that would stimulate a therapeutic angiogenesis response, the method describes a technique for accurately delivering a treatment agent into the wall of the blood vessel or beyond the wall of the blood vessel as the particular situation may dictate. The method utilizes imaging of a thickness of the wall of a blood vessel to accurately place the treatment agent. Suitable imaging techniques include, but are not limited to, ultrasonic imaging, optical imaging, and magnetic resonance imaging.

In another embodiment, a method includes introducing a treatment agent in a sustained release composition or carrier. Treatment agents that can sustain their effectiveness for a period of up to one to ten weeks, preferably two to eight weeks, offer maximum benefit for the stimulation of therapeutic angiogenesis. Methods of inducing coronary or peripheral therapeutic angiogenesis by local delivery of sustained release treatment agents using percutaneous devices are described. Such devices may be intraventricular (coronary) or intravascular (coronary and peripheral).

In another embodiment, a method includes placing a treatment agent in or around a blood vessel or other tissue that stimulates therapeutic angiogenesis by inducing an inflammation response in tissue.

In still another embodiment, a sustained-release composition comprising a treatment agent in a form suitable for transvascular delivery is described. Also, a composition comprising a carrier including a treatment agent and an opsonin-inhibitor coupled to the carrier.

In a further embodiment, an apparatus is described that allows the accurate introduction of a treatment agent in or around a blood vessel. The apparatus includes, for example, a catheter body capable of traversing a blood vessel and a dilatable balloon assembly coupled to the catheter body comprising a balloon having a proximal wall. A needle body is disposed within the catheter body and comprises a lumen having dimensions suitable for a needle to be advanced there through. The needle body includes an end coupled to the proximal wall of the balloon. The apparatus also includes an imaging body disposed within the catheter body and comprising a lumen having a dimension suitable for a portion of an imaging device to be advanced there through. The apparatus further includes a portion of an imaging device disposed within the imaging body adapted to generate imaging signals of the blood vessel, including imaging signals of a thickness of the wall of a blood vessel. An apparatus such as described is suitable for accurately introducing a treatment agent at a desired treatment site in or around a blood vessel.

BRIEF DESCRIPTION OF THE DRAWINGS

The features of the described embodiments are specifically set forth in the appended claims. However, the embodiments are best understood by referring to the following description and accompanying drawings, in which similar parts are identified by like reference numerals.

DETAILED DESCRIPTION

In connection with the description of the various embodiments, the following definitions are utilized:

"Therapeutic angiogenesis" refers to the processes of causing or inducing angiogenesis and arteriogenesis.

"Angiogenesis" is the promotion or causation of the formation of new blood vessels in the ischemic region.

"Arteriogenesis" is the enlargement of pre-existing collateral vessels. The collateral vessels allow blood to flow from a well-perfused region of the vessel into the ischemic region.

"Ischemia" is a condition where oxygen demand of the tissue is not met due to localized reduction in blood flow caused by narrowing or occlusion of one or more vessels. Narrowing of arteries such as coronary arteries or their branches, is most often caused by thrombosis or via deposits of fat, connective tissue, calcification of the walls, or restenosis due to abnormal migration and proliferation of smooth muscle cells.

"Occlusion" is the total or partial obstruction of blood flow through a vessel.

"Treatment agent" includes agents directed to specific cellular binding sites (e.g., receptor binding treatment agents) and agents that induce inflammation.

"Specific binding treatment agent" or "receptor binding treatment agent" includes a protein or small molecule that will induce and/or modulate a therapeutic angiogenic response through interaction with a specific binding site (e.g., a binding within a cell or on a cell surface). Representative treatment agents include, but are not limited to, vascular endothelial growth factor (VEGF) in any of its multiple isoforms, fibroblast growth factors, monocyte chemoattractant protein 1 (MCP-1), transforming growth factor beta (TGF-beta) in any of its multiple isoforms, transforming growth factor alpha (TGF-alpha), lipid factors, hypoxia-inducible factor 1-alpha (HIF-1-alpha), PR39, DEL 1, nicotine, insulin-like growth factors, placental growth factor (PlGF), hepatocyte growth factor (HGF), estrogen, follistatin, proliferin, prostaglandin E1, prostaglandin E2, cytokines, tumor necrosis factor (TNF-alpha), erythropoietin, granulocyte colony-stimulating factor (G-CSF), granulocyte macrophage colony-stimulating factor (GM-CSF), angiogenin, hormones, and genes that encode such substances.

"Non-specific treatment agent" includes, as described in more detail herein, various agents that induce inflammation.

"Carrier" includes a matrix that contains one or more treatment agents. A suitable carrier may take the form of a nanoparticle (e.g., nanosphere) or microparticle (e.g., microsphere) as the situation may dictate.

Figure 1:
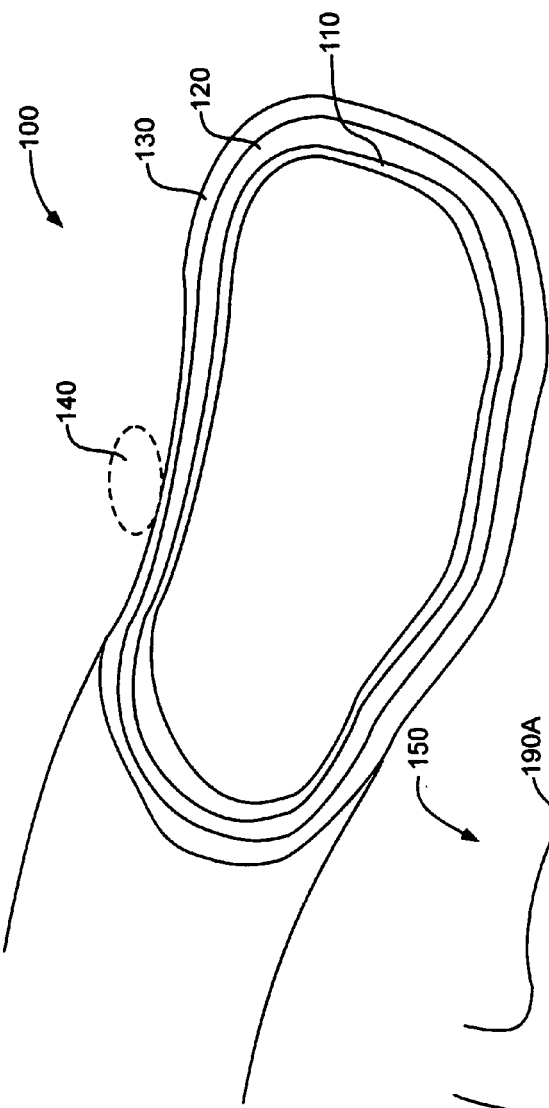
FIG. 1 schematically illustrates a perspective and cross-section view of a blood vessel.

Referring to FIG. 1, a non-diseased artery is illustrated as a representative blood vessel. Artery 100 includes an arterial wall having a number of layers. Innermost layer 110 is generally referred to as the intimal layer that includes the endothelium, the subendothelial layer, and the internal elastic lamina. Medial layer 120 is concentrically outward from intimal layer 110 and bounded by external elastic lamina and adventitial layer 130 is the outermost layer. There is no external elastic lamina in a vein. Medial layer 120 (in either an artery or vein) primarily consists of smooth muscle fibers and collagen. Beyond medial layer 120 and adventitial layer 130 lies the extravascular tissue including, adjacent adventitial layer 120 (and possibly including a portion of adventitial layer 120), area 140 referred to as peri-adventitial site (space) or area. Areas radially outward from a peri-adventitial space include connective tissue such as adipose tissue that is most likely located, in terms of areas around the heart, toward the epicardial surface of the heart and myocardial tissue composed of muscle fibers.

Figure 2:
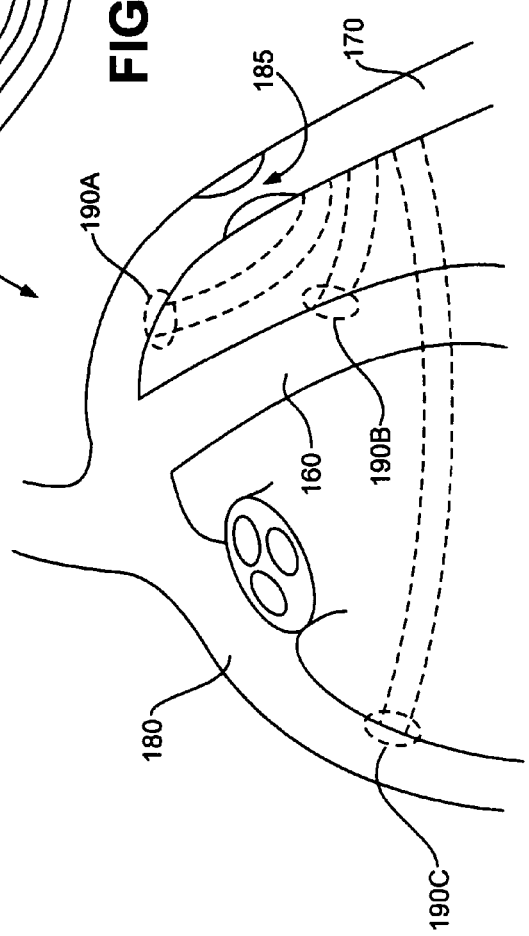
FIG. 2 schematically illustrates a planar cross-sectional view of components of a coronary artery network.

FIG. 2 illustrates components of a coronary artery network. In this simplified example, vasculature 150 includes left anterior descending artery (LAD) 160, left circumflex artery (LCX) 170 and right coronary artery (RCA) 180. Sites 190A, 190B, and 190C are preferably in the peri-adventitial space or radially outward from the peri-adventitial space (e.g., in adipose or myocardial tissue). Occlusion 185 is shown in LCX 170. Occlusion 185 limits the amount of oxygenated blood flow through LCX 170 to the myocardium that it supplied, resulting in ischemia of this tissue.

To improve the function of the artery network, it is generally desired to either remove occlusion 185 (for example through an angioplasty procedure), bypass occlusion 185 or induce therapeutic angiogenesis to makeup for the constriction and provide blood flow to the ischemic region (e.g., downstream of occlusion 185). FIG. 2 shows therapeutic angiogenesis induced at sites 190A (associated with LCX 170); 190B (associated with LAD 160); and 190C (associated with RCA 180). By inducing therapeutic angiogenesis at sites 190A, 190B, and 190C, permanent revascularization of the network is accomplished, thus compensating for reduced flow through LCX 170. The following paragraphs describe compositions, techniques and an apparatus suitable for inducing therapeutic angiogenesis.

A. Specific Binding Treatment Agents

In one embodiment, therapeutic angiogenesis is induced and modulated by locally delivering a treatment agent in a sustained-release carrier. The sustained-release carrier comprising a treatment agent may be strategically placed, for example, along an occlusion to produce an angiogenic concentration gradient to encourage the specific directional growth or expansion of collateral vessels. For example, in reference to FIG. 2, treatment agents placed at zone 190A, above (as viewed) occluded vessel LCX 170 are selected such that, while up-stream, a therapeutic angiogenic or arteriogenic response will encourage growth of collaterals around occlusion 185 meeting up with LCX 170 down-stream of the occlusion. Similarly, a treatment agent strategically placed at a location in a region near to left coronary artery 160 (e.g., region 190B) will encourage bridging of collateral vessels, in this case, between left coronary artery 160 and LCX 170. Similar encouragement and bridging may be obtained by strategically placing a treatment agent at a region of RCA 180 (such as region 190C). While the application of therapeutic angiogenesis to alleviating ischemia resulting from a flow limiting obstruction in the LCX is described, those familiar with the art will appreciate that the method described is applicable to the treatment of flow limiting obstructions in other coronary vessels and in the peripheral vasculature.

Suitable treatment agents include specific binding or receptor binding treatment agents. Suitable sustained-release carriers encapsulating the specific binding agents may take the form of polymer nanoparticles or microparticles, typically in the form of nanospheres or microspheres, having an average particle size less than 100 microns (µm) and preferably less than about 10 µm to, in one aspect, enable delivery through a catheter equipped with an injection needle. Sustained release of treatment agents for a period of up to one to ten weeks, preferably up to two to eight weeks is believed to offer maximum benefit for the stimulation of therapeutic angiogenesis. In another embodiment, the sustained release of treatment agents over a period of one day or longer is preferred. The loading of the receptor binding treatment agent in the sustained release carrier is in the range of about 0.5 percent to about 30 percent weight by volume (w/v), and the total dose of the receptor binding treatment agent delivered to the treatment location is in the range of about 1 microgram (µg) to about 1 gram (g).

Sustained release microparticle formulations with different release rates may be delivered in combination to achieve multi-modal release profiles over a period of time.

B. Non-Specific Treatment Agents

As stated above, specific binding or receptor binding treatment agents can induce therapeutic angiogenesis. One embodiment of another suitable treatment agent that will induce and/or modulate a therapeutic angiogenic response is an inflammation-inducing agent. Studies have shown that tissue, including blood vessels, respond to injury induced by implanting foreign materials in three broad phases. The first phase is characterized by minimal inflammatory reaction, with the presence of a few lymphocytes, plasma cells, monocytes, and polymorphonuclear leukocytes. The response to injury in this first phase is determined primarily by the extent of injury caused, for example, by a needle of a needle catheter contacting a blood vessel and the volume of therapeutic substance (e.g., treatment agent) injected to the site of interest. The second response to injury phase is characterized by a predominance of monocytes and macrophages. In the case of biodegradable implants, the duration of this second phase is determined by the rate of biodegradation of the carrier. During this phase, monocytes differentiate into macrophages at the site of injury and the macrophages themselves fuse into foreign body "giant" cells. Fibroblast infiltration and neoangiogenesis are also observed at this stage. For biodegradable implants, there is a third response to injury phase, characterized by the breakdown of the biodegradable material. In this phase, macrophages predominate at the site of implantation. The extent of inflammation and the concentration of monocyte/macrophages at the implantation site reaches a peak at this third phase. Monocyte accumulation and activation is thought to be a potent means of inducing therapeutic angiogensis In one embodiment, ischemic regions supplied by a blood vessel such as ischemic region caused by a lesion in the LCX 170 in FIG. 2 may be treated by implantation of an inflammation-inducing agent (a "non-specific" agent) optionally combined with or contained in (encapsulated) a sustained-release carrier. The implantation may be accomplished non-invasively through, for example, catheter-based technologies, minimally invasively, or in conjunction with surgical procedures. The extent and duration of inflammation is dependent on the non-specific agent being implanted. A combination of agents may be implanted to modulate the extent of inflammation over a period of time, which is typically on the order of about two weeks to about eight weeks.

Suitable inflammation-inducing agents include, but are not limited to, (1) bioresorbable inorganic compounds such as sol gel particles and calcium phosphate glass comprising iron; (2) fibrin, gelatin, low molecular weight hyaluronic acid, and chitin; (3) bacterial polysaccharides; (4) metals; and (5) certain other polymers (which themselves may function as both treatment agent and carrier, including a sustained-release carrier) including bioresorbable polymers such as polycaprolactone (PCL), polyhydroxybutyrate-valerate (PHBV), poly (oxy)ethylene (POE), and non-bioresorbable polymers such as polyurethanes and silicones. The inflammation-inducing treatment agent may be combined as a composition with one or more other specific binding or receptor binding treatment agents that are believed to induce therapeutic angiogenesis such as growth factors.

Representative examples of inflammation-inducing treatment agents that may be combined, in one embodiment, with a sustained release carrier include the following.

Silica sol gel particles, such as manufactured by Bioxid LTD OY of Turku, Finland, are bioresorbable inorganic compounds that can be pro-inflammatory on their own and also serve as a drug eluting reservoir for other pro-inflammatory agents (e.g., lipopolysaccharides (LPS), chitin, etc.). Calcium-phosphate glass containing iron will degrade in a humid environment as a function of the iron composition, resulting in an absorbable glass. One example of absorbable glass is made by MOSCI, Inc. of Rolla, Mo. The absorbable glass may induce controlled inflammation by the physical dimension of the degradation product. A combination of PLGA coated (with or without activation) or partially coated absorbable glass may be employed to modulate the degradation rate of different species.

Chitin is a polysaccharide derived principally from crab shells, and shows a pro-inflammatory reaction. Micronized chitin can be incorporated into microspheres or disbursed into a polymer system such as described above to enhance the inflammatory action of treatment agent of microspheres or precipitated polymers. The micronized chitin can also be disbursed in a gel that may then be extruded via a needle catheter to a desired treatment location (within the vascular or myocardium). Gelatin (a partially degraded form of collagen) and fibrin may be utilized in a similar manner.

The outer membranes of gram-negative bacteria containing lipopolysaccharides (LPS) can be pro-inflammatory. Isolation of LPS and incorporation into degradeable microspheres can enhance the inflammatory reaction of the microspheres and provide a more potent angiogenic action.

The cell walls of blood vessels are typically rich in glycocalyx and other specific antigens. Systemic immune response may be upregulated by administration of vaccines or denatured proteins such as Ab, Fb, etc. In another embodiment, the localized introduction (e.g., through a catheter) of vaccines or certain denatured proteins may be used in combination with, for example, inflammatory-inducing treatment agents to potentiate the controlled inflammatory effect Particles of metal such as gold (Au) and titanium (Ti) are known to induce inflammation and activate monocytes. These particles may be injected as a suspension at a local site of interest via, for example, a needle catheter. To amplify an effect, such thermally conductive particles can be heated with, for example, using a 900 to 1200 nanometer (nm) range remote source of radio frequency energy to further cause controlled damage to the tissue resulting in inflammation and promoting therapeutic angiogenesis; 10 to 100 nanometer (nm) spherical particles are shown to have this remote activatible heating effect.

C. Methods of Forming Sustained Release Particles

In the previous paragraphs, both specific binding treatment agents and non-specific binding treatment agents have been described in conjunction with promoting therapeutic angiogenesis. Such promotion is encouraged, in one embodiment, by delivering the treatment agent in or with a sustained-release carrier. Suitable materials for sustained-release carriers include, but are not limited to, encapsulation polymers such as poly (L-lactide), poly (D,L-lactide), poly (glycolide), poly (lactide-co-glycolide), polycaprolactone, polyanhydride, polydiaxanone, polyorthoester, polyamino acids, or poly (trimethylene carbonate), and combinations thereof. To form a sustained-release carrier composition of, for example, microparticles or nanoparticles (e.g., microspheres or nanospheres) comprising one or more treatment agents including a non-specific treatment agent and/or a specific binding agent, the following techniques may be used.

1. Solvent Evaporation

In this method, the polymer is dissolved in a volatile organic solvent such as methylene chloride. The treatment agent is then added to the polymer solution either as an aqueous solution containing an emulsifying agent such as polyvinyl alcohol (PVA), or as a solid dispersion, and stirred, homogenized or sonicated to create a primary emulsion of protein in the polymer phase. This emulsion is stirred with an aqueous solution containing an emulsifying agent such as PVA to create a secondary emulsion of treatment agent containing polymer in the aqueous phase. This emulsion is stirred in excess water, optionally under vacuum to remove the organic solvent and harden the particles. The hardened particles are collected by filtration or centrifugation and lyophillized. A desired particle size (e.g., microparticle or nanoparticle) may be selected by varying the preparation conditions (e.g., viscosity of the primary emulsion, concentration of the treatment agent, mixing (shear) rate, etc.). The particles tend to adopt a spherical shape in response to minimizing surface tension effects.

2. Coacervation:

In this method, a primary emulsion of treatment agent in an aqueous phase is formed as in the solvent evaporation method. This emulsion is then stirred with a non-solvent for the polymer, such as silicone oil to extract the organic solvent and form embryonic particles of polymer with trapped treatment agent. The non-solvent is then removed by the addition of a volatile second non-solvent such as heptane, and the particles hardened. The hardened particles are collected by filtration or centrifugation and lyophillized. Again, the particle size may be selected as described above with reference to solvent evaporation.

3. Spray Drying:

In this method, the treatment agent, formulated as lyophilized powder is suspended in a polymer phase consisting of polymer dissolved in a volatile organic solvent such as methylene chloride. The suspension is then spray dried to produce polymer particles with entrapped treatment agent. The particle size may be selected as described above with reference to solvent evaporation.

4. Cryogenic Process:

In this method, the treatment agent, formulated as lyophillized powder is suspended in a polymer phase consisting of polymer dissolved in a volatile organic solvent such as methylene chloride. The suspension is sprayed into a container containing frozen ethanol overlaid with liquid nitrogen. The system is then warmed to −70° C. to liquify the ethanol and extract the organic solvent from the treatment agent particles. The hardened microspheres are collected by filtration or centrifugation and lyophillized.

5. In situ Process:

Sustained release carriers (e.g., microparticles and/or nanoparticles) may be formed before introduction (e.g., injection) into the blood vessel as described above, or they may be formed in situ. One way to form such particles in situ is by co-desolving a treatment agent and a matrix forming polymer in a water miscible solvent such as dimethyl sulfoxide (DMSO), N-methylpyrrolidone (NMP), ethanol or glycofural and injecting the solution at the site of treatment with, for example, a catheter to precipitate out polymer particles. Several polymer solutions, each consisting of a polymer formulation with a different degradation rate can be injected in sequence to precipitate out a mixed population of polymer particles, in order to obtain a multi-modal release profile.

6. Example of Loading and Dose for Inducing/Modulating Therapeutic Angiogenesis As noted above, one example of the preparation of nanoparticles (e.g., nanospheres) or microparticles (e.g., microspheres) suitable for use in therapeutic angiogenesis is in the form of a solution. Nanoparticles or microparticles may be loaded with specific or non-specific agents in the range of 0.5-30 percent w/v. In the case of inflammatory agents, loading may be as high as 100 percent w/v. A suitable dose may be calculated as follows:

DOSE=number of injectionsx% suspension of nano- and/or microparticles[(weight of nano- and/or microparticles)/volume of solution]×volume of solutionx% loading[weight of agent/(weight of nano- and/or microparticles)].

Using an inflammatory treatment agent such as gold particles as an example, loading may be 100 percent. In 0.2 ml solution five percent w/v of particles provides for maximal dose of 10 micrograms of material per injection. The number of injections is determined by an operator. The total dose is in the range of 1 microgram to 1 gram. It is to be appreciated that the optimal dose may be determined in a relevant animal model of ischemia by delivering the nano- and/or microparticle suspension through a needle catheter or simply by injecting during open-heart procedure and generating a dose-response curve.

D. Compositions Having a Particle Size of 10 Microns or Less

Treatment agents, including treatment agents combined with a carrier (e.g., a sustained release carrier), having a particle size greater than approximately 10 microns have the potential, when introduced into the arterial vascular system, of being trapped in the capillary bed. Trapping large numbers of microparticles in the capillary bed could result in ischemia. Treatment agent compositions having particle diameters less than about 10 microns, however, are rapidly phagocytosed, resulting in reduced availability of the treatment agent at target sites, where, for example, sustained-released of the treatment agent may be desired in a certain therapeutic concentration range.

Regarding phagocytosis, when a foreign material is implanted into a host tissue, the first event to occur at the tissue-material interface is the adsorption of plasma proteins from blood onto the surface of the foreign material. Opsonins are plasma proteins, such as complement and immunoglobulin, that adhere to foreign materials such as nanoparticles and facilitate their phagocytosis through the recognition of the adsorbed opsonins by macrophages of the reticulo-endothelial system. Microspheres larger than about 10 microns are also opsonized, but are generally considered too large to be phagocytosed.

In one embodiment, the treatment agent compositions suitable for therapeutic angiogenesis are rendered resistant to phagocytosis by inhibiting opsonin protein adsorption to the composition particles. In this regard, treatment agent compositions including sustained release carriers comprise particles having an average diameter of up to about 10 microns are contemplated.

One method of inhibiting opsonization and subsequent rapid phagocytosis of treatment agents is to form a composition comprising a treatment agent disposed within a carrier (e.g., a sustained release carrier) and to coat the carrier with an opsonin inhibitor. One suitable opsonin-inhibitor includes polyethylene glycol (PEG) which creates a brush-like steric barrier to opsonization. PEG may alternatively be blended into the polymer constituting the carrier, or incorporated into the molecular architecture of the polymer constituting the carrier, as a copolymer, to render the carrier resistant to phagocytosis. Examples of preparing the opsonin-inhibited microspheres include the following.

For the encapsulation polymers, a blend of a polyalkylene glycol such as polyethylene glycol (PEG), polypropylene 1,2-glycol or polypropylene 1,3-glycol is co-dissolved with an encapsulating polymer in a common organic solvent during the carrier forming process. The percentage of PEG in the PEG/encapsulating polymer blend is between five percent and 60 percent by weight. Other hydrophilic polymers such as polyvinyl pyrolidone, polyvinyl alchohol, or polyoxyethylene-polyoxypropylene copolymers can be used in place of polyalkylene glycols, although polyalkylene glycols and more specifically, polyethylene glycol is generally preferred.

Alternatively, a diblock or triblock copolymer of an encapsulating polymer such as poly (L-lactide), poly (D,L-lactide), or poly (lactide-co-glycolide) with a polyalkylene glycol may be prepared. Diblocks can be prepared by: (i) reacting the encapsulating polymer with a monomethoxy polyakylene glycol such as PEG with one protected hydroxyl group and one group capable of reacting with the encapsulating polymer, (ii) by polymerizing the encapsulating polymer on to the monomethoxy polyalkylene glycol such as PEG with one protected group and one group capable of reacting with the encapsulating polymer; or (iii) by reacting the encapsulating polymer with a polyalkylene glycol such as PEG with amino functional termination. Triblocks can be prepared as described above using branched polyalkylene glycols with protection of groups that are not to react. Opsonization resistant carriers (microparticles/nanoparticles) can also be prepared using the techniques described above to form sustained-release carriers (microparticles/nanoparticles) with these copolymers.

A second way to inhibit opsonization is the biomimetic approach. For example, the external region of cell membrane, known as the "glycocalyx", is dominated by glycoslylated molecules which prevent non-specific adhesion of other molecules and cells. Surfactant polymers consisting of a flexible poly (vinyl amine) backbone randomly-dextran and alkanoyl (hexanoyl or lauroyl) side chains which constrain the polymer backbone to lie parallel to the substrate. Hydrated dextran side chains protrude into the aqueous phase, creating a glycocalyx-like monolayer coating which suppresses plasma protein deposition on the foreign body surface. To mimic glycocalyx, glycocalyx-like molecules can be coated on the carriers (e.g., nanoparticles or microparticles) or blended into a polymer constituting the carrier to render the treatment agent resistant to phagocytosis. An alternate biomimetic approach is to coat the carrier with, or blend in phosphorylcholine, a synthetic mimetic of phosphatidylcholine, into the polymer constituting the carrier.

For catheter delivery, a carrier comprising a treatment agent (e.g., the composition in the form of a nanoparticle or microparticle) may be suspended in a fluid for delivery through the needle, at a concentration of about one percent to about 20 percent weight by volume. In one embodiment, the loading of the treatment agent in a carrier is about 0.5 percent to about 30 percent by weight of the composition. Co-encapsulated with protein or small molecule angiogen treatment agents could be stabilizers that prolong the biological half-life of the treatment agent in the carrier upon injection into tissue. Stabilizers may also be added to impart stability to the treatment agent during encapsulation. Hydrophilic polymers such as PEG or biomimetic brush-like dextran structures or phosphorylcholine are either coated on the surface or the carrier, grafted on the surface of the carrier, blended into the polymer constituting the carrier, or incorporated into the molecular architecture of the polymer constituting the carrier, so the carrier is resistant to phagocytosis upon injection into the target tissue location.

E. Catheter Assembly

One concern of introducing sustained-release treatment agent compositions into or adjacent blood vessels or the myocardium is that the composition remain (at least partially) at the treatment site for the desired treatment duration (e.g., two to eight weeks). Accordingly, in another embodiment, an apparatus (a catheter assembly) is described for accurately locating a treatment agent at a location in a blood vessel (preferably beyond the media layer) or in a peri-adventitial space adjacent to a blood vessel, or areas radially outward from a peri-adventitial space, or at tissue location such as the tissue of the myocardium. It is appreciated that a catheter assembly is one technique for introducing treatment agents and the following description is not intended to limit the application or placement of the treatment agent compositions described above.

Figure 3:
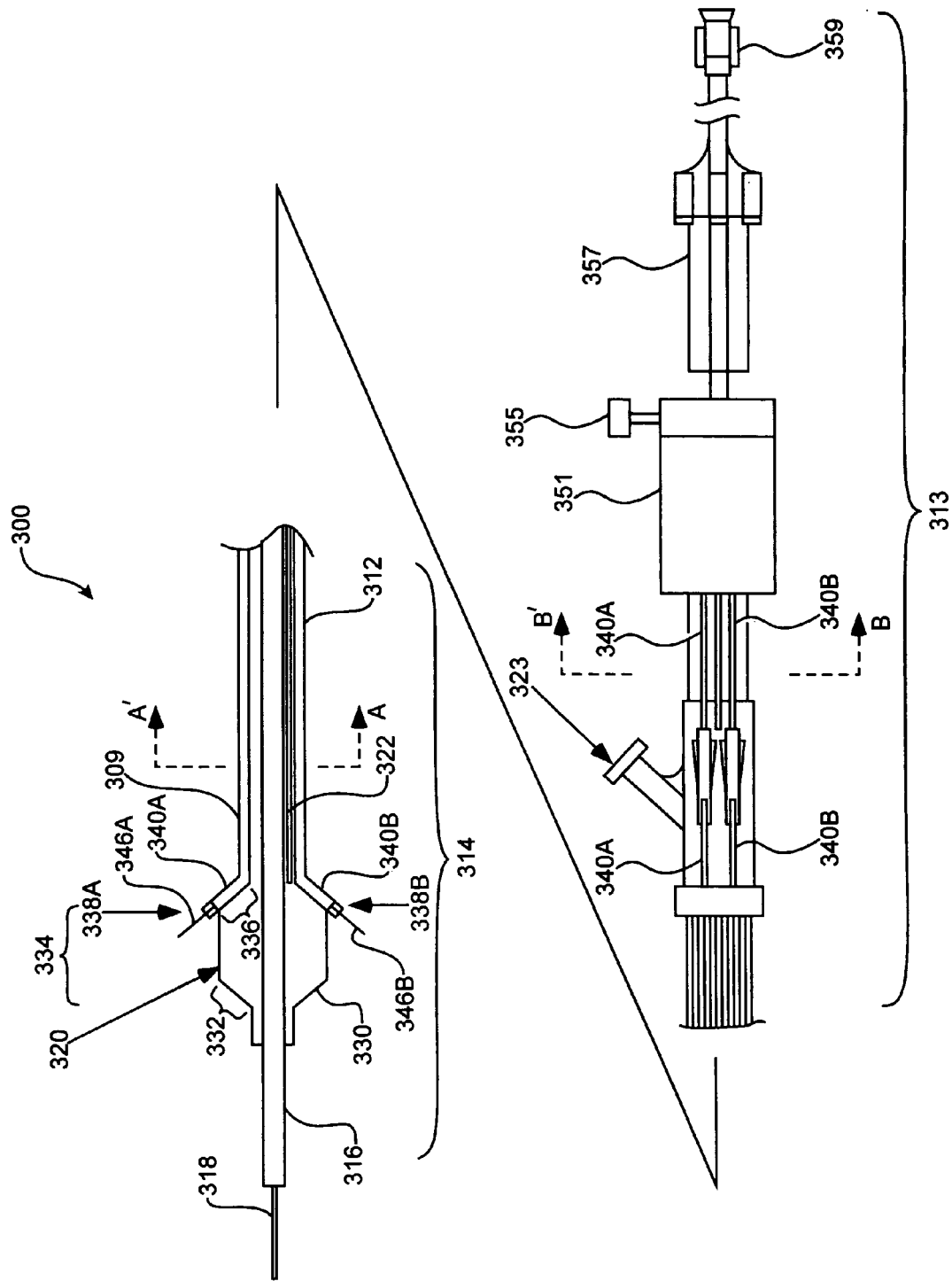
FIG. 3 is a simplified cross-sectional view of an embodiment of a substance delivery apparatus in the form of a catheter assembly having a balloon and a therapeutic substance delivery assembly.
Figure 4:
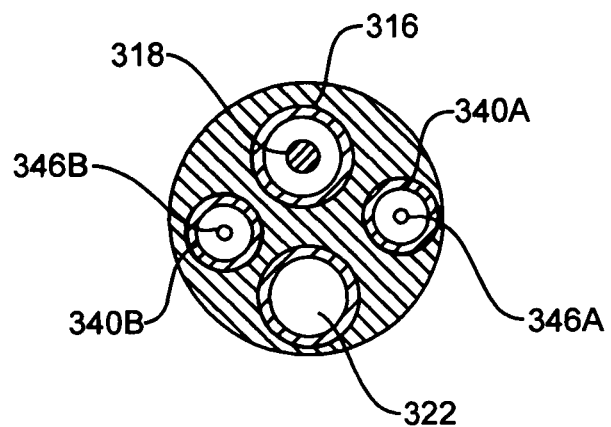
FIG. 4 schematically illustrates a planar cross-section of the substance delivery apparatus of FIG. 3 through line A-A'.
Figure 5:
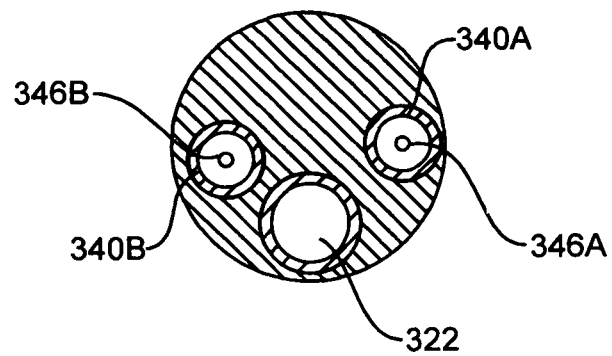
FIG. 5 schematically illustrates a planar cross-section of the substance delivery apparatus of FIG. 3 through line B-B'.

Referring now to the drawings, wherein similar parts are identified by like reference numerals, FIGS. 3, 4, and 5 illustrate one embodiment of a delivery apparatus. In general, the delivery apparatus provides a system for delivering a substance, such as a treatment agent or a combination of treatment agents optionally presented as a sustained release composition, to or through a desired area of a blood vessel (a physiological lumen) or tissue in order to treat a localized area of the blood vessel or to treat a localized area of tissue possibly located adjacent to the blood vessel. The delivery apparatus is similar in certain respects to the delivery apparatus described in commonly-owned, U.S. patent application Ser. No. 09/746,498 (filed Dec. 21, 2000), titled "Directional Needle Injection Drug Delivery Device", of Chow, et al., and incorporated herein by reference. The delivery apparatus includes a catheter assembly 300, which is intended to broadly include any medical device designed for insertion into a blood vessel or physiological lumen to permit injection and/or withdrawal of fluids, to maintain the potency of the lumen, or for any other purpose.

In one embodiment, catheter assembly 300 is defined by elongated catheter body (cannula) 312 having proximal end 313 and distal end 314. FIG. 4 shows catheter assembly 300 through line A-A' of FIG. 3 (at distal end 314). FIG. 5 shows catheter assembly 300 through line B-B' of FIG. 3 (at proximal end 313).

Referring to FIG. 3 and FIG. 4, catheter assembly 300 includes catheter body 312 extending from proximal end 313 to distal end 314. In this example, guidewire lumen 316 is formed within catheter body 312 for allowing catheter assembly 300 to be fed and maneuvered over guidewire 318 (shown at this point within guidewire lumen 316).

Balloon 320 is incorporated at distal end 314 of catheter assembly 300 and is in fluid communication with inflation lumen 322 formed within catheter body 312 of catheter assembly 300. Balloon 320 includes balloon wall or membrane 330 which is selectively inflatable to dilate from a collapsed configuration to a desired and controlled expanded configuration. Balloon 320 can be selectively dilated (inflated) by supplying a fluid into inflation lumen 322 at a predetermined rate of pressure through inflation port 323. Balloon wall 330 is selectively deflatable, after inflation, to return to the collapsed configuration or a deflated profile. In one embodiment, balloon wall 330 can be defined by three sections, distal taper wall 332, medial working length 334, and proximal taper wall 336. In one embodiment, proximal taper wall 336 can taper at any suitable angle θ, typically between about 10° to less than about 90°, when balloon 320 is in the expanded configuration.

Distal taper wall 332, medial working length 334, and proximal taper wall 336 of balloon wall 330 can be bound together by seams or be made out of a single seamless material. Balloon 320 can be made from any suitable material, including, but not limited to, polymers and copolymers of polyolefins, polyamides, polyesters and the like. The specific material employed must be mutually compatible with the fluids employed in conjunction with balloon 320 and must be able to stand the pressures that are developed within balloon 320. Balloon wall 330 can have any suitable thickness so long as the thickness does not compromise properties that are critical for achieving optimum performance. Such properties include high burst strength, low compliance, good flexibility, high resistance to fatigue, the ability to fold, the ability to cross and re-cross a desired region of treatment or an occluded region in a lumen, and low susceptibility to defect caused by handling. By way of example, and not limitation, the thickness can be in the range of about 10 microns to about 30 microns, the diameter of balloon 320 in the expanded configuration can be in the range of about 2 millimeters (mm) to about 10 mm, and the length can be in the range of about 3 mm to about 40 mm, the specific specifications depending on the procedure for which balloon 320 is to be used and the anatomy and size of the target lumen in which balloon 320 is to be inserted.

Balloon 320 may be dilated (inflated) by the introduction of a liquid into inflation lumen 322. Liquids containing therapeutic and/or diagnostic agents may also be used to inflate balloon 320. In one embodiment, balloon 320 may be made of a material that is permeable to such therapeutic and/or diagnostic liquids. To inflate balloon 320, the fluid can be supplied into inflation lumen 322 at a predetermined pressure, for example, between about one and 20 atmospheres.

Catheter assembly 300 also includes substance delivery assembly 338A and substance for injecting a treatment agent into a tissue of a physiological passageway. In one embodiment, delivery assembly 338A includes needle 346A having a lumen with a diameter of, for example, 0.004 inches (0.010 cm) to 0.012 inches (0.030 cm). Needle 346A is movably disposed within delivery lumen 340A formed in catheter body 312. Delivery assembly 338B includes needle 346B movably disposed within delivery lumen 340B formed in catheter body 312. Delivery lumen 340A and delivery lumen 340B each extend between distal end 314 and proximal end 313. Delivery lumen 340A and delivery lumen 340B can be made from any suitable material, such as polymers and copolymers of polyamides, polyolefins, polyurethanes, and the like. Access to the proximal end of delivery lumen 340A or delivery lumen 340B for insertion of needle 346A or 346B, respectively is provided through hub 351.

One or both of delivery lumen 340A and delivery lumen 340B may be used to deliver a treatment agent to a treatment site (e.g., through needle 346A and/or needle 346B). Alternatively, one delivery lumen (e.g., delivery lumen 340A via needle 346A) may be used to deliver a treatment agent (e.g., therapeutic angiogenic treatment agent) while the other delivery lumen (e.g., delivery lumen 340B via needle 346B) may be used to deliver a therapeutic substance that is a non-therapeutic angiogenic substance.

Catheter assembly 300 also includes an imaging assembly. Suitable imaging assemblies include ultrasonic imaging assemblies, optical imaging assemblies, such as an optical coherence tomography (OCT) assembly, magnetic resonance imaging (MRI). FIGS. 3-5 illustrate an embodiment of a catheter assembly, including an OCT imaging assembly.

Figure 8:
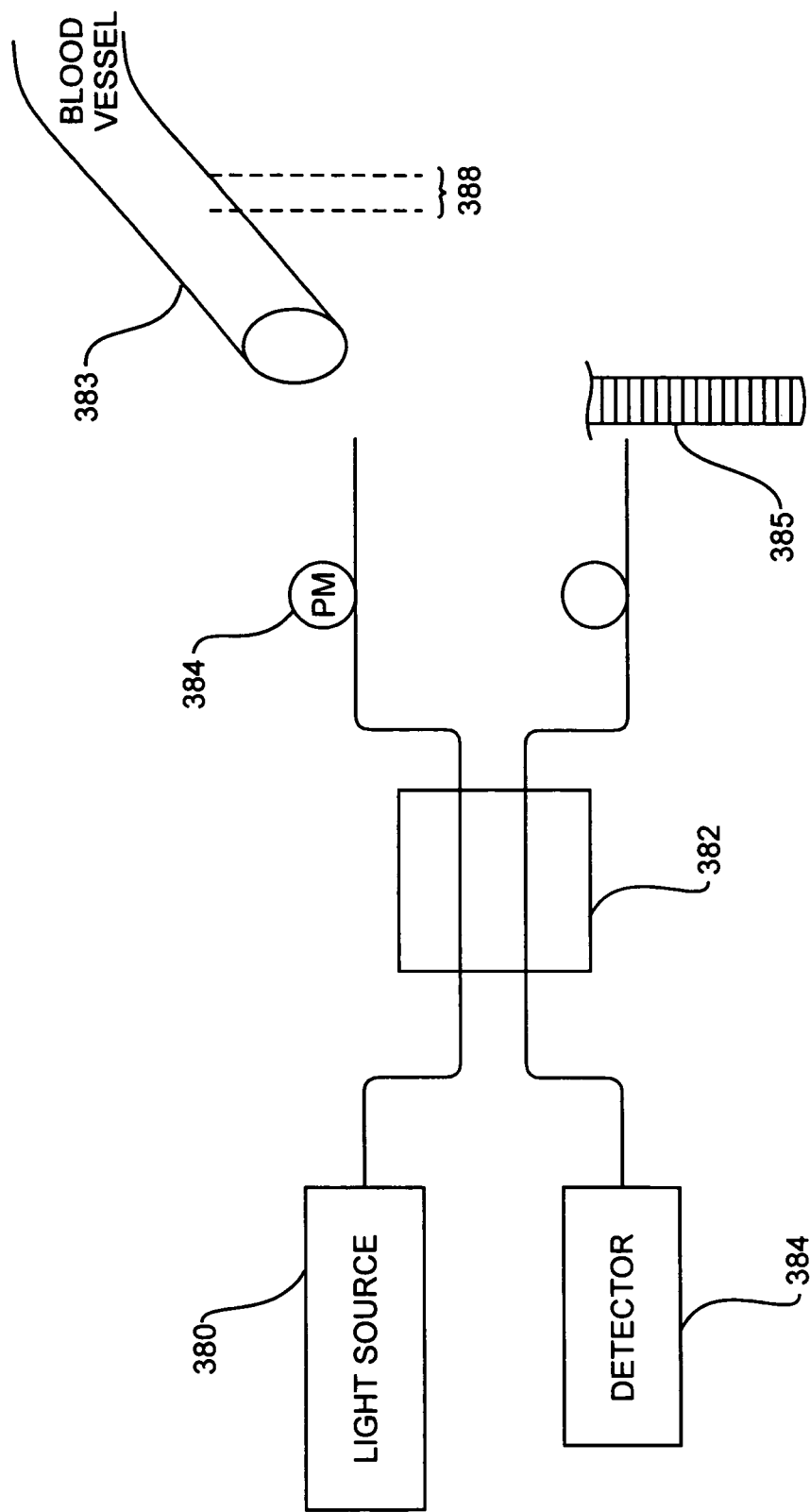
FIG. 8 schematically illustrates an optical imaging system for use in a substance delivery apparatus such as a catheter assembly.

OCT uses short coherence length light (typically with a coherent length of about 10 to 100 microns) to illuminate the object (e.g., blood vessel or blood vessel walls). Light reflected from a region of interest within the object is combined with a coherent reference beam. Interference occurs between the two beams only when the reference beam and reflective beam have traveled the same distance. FIG. 8 shows one suitable OCT setup similar in some respects to ones disclosed in U.S. Pat. Nos. 5,465,147; 5,459,570; 5,321,501; 5,291,267; 5,365,325; and 5,202,745. A suitable optical assembly for use in conjunction with a catheter assembly is made with fiber optic components that, in one embodiment, can be passed through the guidewire lumen (e.g., guidewire lumen 316 of FIG. 3). Light having a relatively short coherence length, $l_c$ (given by $l_c = C/\Delta f$, where $\Delta f$ is the spectral bandwidth) is produced by light source 380 (e.g., incandescent source, laser source or light emitting diode of suitable wavelength) and travels through 50/50 coupler 382 where it is divided into two paths. One path goes to blood vessel 383 to be analyzed and the other path goes to a moveable reference mirror 385. The probe beam reflected from sample 383 and the reference beam reflected from reference mirror 385 are combined at coupler 382 and sent to detector 387. The optical path traversed by the reflected probe beam and the reference beam are matched to within one coherence length such that coherent interference can occur upon recombination at coupler 382.

Phase modulator 384 produces a temporal interference pattern (beats) when recombined with the reference beam. Detector 387 measures the amplitude of the beats. The amplitude of the detected interference signal is the measure of the amount of light scattered from within a coherence gate interval 388 inside, in this case, blood vessel 383 that provides equal path lengths for the probe and reference beams. Interference is produced only for light scattered from blood vessel 383 which has traveled the same distance as light reflected from mirror 385.

In one embodiment, the optical fiber portion of the OCT imaging system can be inserted in the guidewire lumen of an over the wire catheter with guidewire lumen terminating at the imaging wire coupling. The body of the guidewire lumen (e.g., body of lumen 316 of the assembly of FIG. 3) and the body of the balloon assembly (e.g., body 330 of balloon assembly in FIG. 3) should be transparent at the distal end to allow optical imaging through the body of the lumen (e.g., through the body of balloon 320). Thus, once the catheter assembly is placed, at a desired location within, for example, a blood vessel, guidewire 318 may be removed and replaced with an optical fiber. In a catheter assembly such as illustrated in FIG. 3, the replacement of the guidewire with an optical fiber is done, in one embodiment, at low inflation pressure of balloon 320.

Where an optical fiber is substituted for a guidewire, the dimensions of a catheter does not have to be modified. Optical fibers having an outer diameter of 0.014, 0.018, or 0.032 inches (0.36, 0.46, or 0.81 mm, respectively) are suitable for current guidewire lumens. Other imaging components (e.g., fiber rotator, imaging screen, OCT system components, etc.) may be coupled to the optical fiber as it extends out hub 316 at a proximal end of the catheter assembly (e.g., at proximal end 313 of catheter assembly 300). Such components include, but are not limited to, a drive coupling that provides rotation and forward/reverse movement of the optical fiber; a detector, and an imaging screen.

Figure 9:
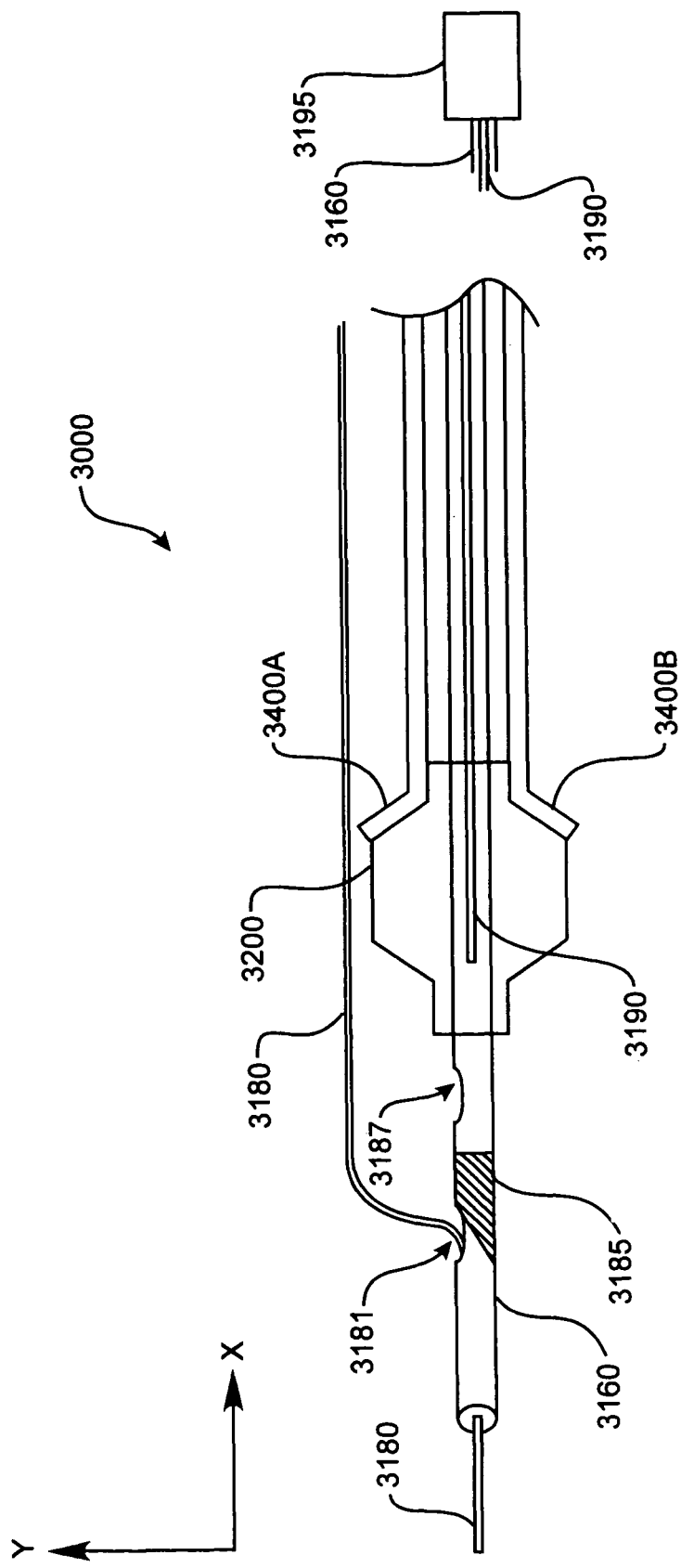
FIG. 9 schematically illustrates a cross-sectional side view of components of an alternative catheter assembly including an optical imaging system.

FIG. 9 shows another embodiment of a catheter assembly including an OCT apparatus. In this embodiment, guidewire 3180 and optical fiber 3190 "share" common imaging lumen 3160. Imaging lumen 3160 is preferably made of a transparent material at the distal end utilized by optical fiber 3190. Catheter assembly 3000 also includes balloon 3200 with needle lumens 3400A and 3400B coupled to a proximal portion of balloon 3200.

Referring to FIG. 9, guidewire 3180 exits imaging lumen 3160 at distal tip 3181 (i.e., distal to balloon 3200). Guidewire 3180 and optical fiber 3190 are separated in imaging lumen 3160 by plug 3185 of, for example, a polymer or copolymer material, having dimensions suitable to fill the lumen. Suitable polymers include polyimides, polyurethanes, and polyolefins. A portion of plug 3185 may also serve as a ramp for guidewire exit port 3180. In this embodiment, imaging of a blood vessel (e.g., imaging of a wall of a blood vessel for thickness determination) is accomplished from a portion of imaging lumen corresponding with the location of balloon 3200. Thus, balloon 3200 is also preferably made of a transparent material. Flush port 3187 may also be included for clearing imaging portion of imaging lumen 3160.

At a proximal end, imaging lumen 3160 of FIG. 9 terminates in drive coupling 3195. Drive coupling 3195 provides rotation and forward/reverse direction movement of optical fiber 3190 and connection to the OCT system.

In another embodiment, the imaging assembly is based on ultrasonic technology. Ultrasonic systems are referenced in U.S. Pat. Nos. 4,794,931; 5,000,185; 5,049,130; 5,485,486; 5,827,313; and 5,957,941. In one example, an ultrasonic imaging assembly, representatively including an ultrasonic transducer, may be exchanged for a guidewire through a guidewire lumen such as described above with reference to the first OCT embodiment. In another embodiment, a guidewire and ultrasonic transducer "share" a common imaging lumen similar to the embodiment described with reference to FIG. 9 and the accompanying text. In either example, imaging of, for example, a blood vessel will take place through the balloon. In the case of ultrasonic imaging, the balloon and guidewire lumen need not be transparent.

Figure 6:
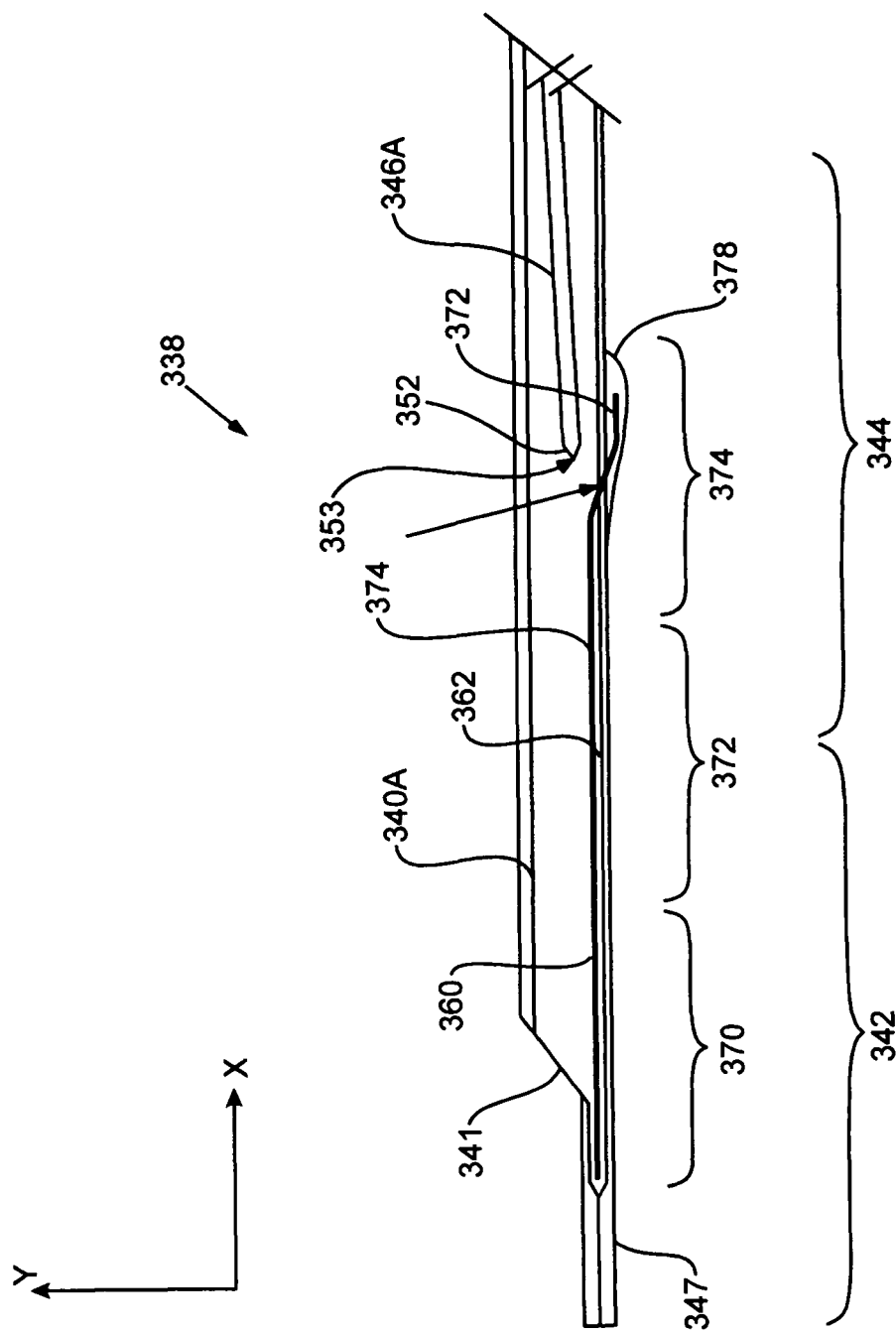
FIG. 6 schematically illustrates a cross-sectional view of the distal section of the substance delivery apparatus of FIG. 3 with the balloon in an undeployed configuration.
Figure 7:
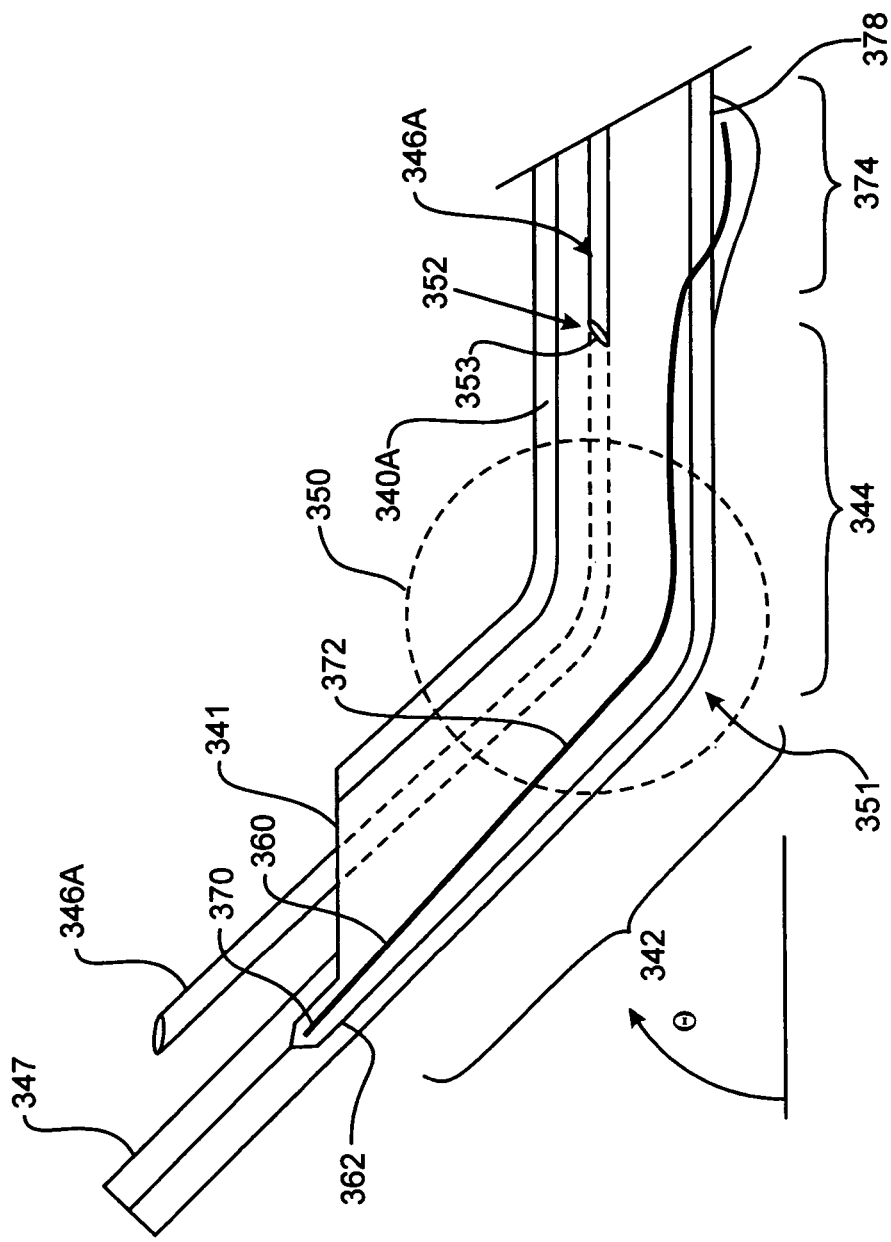
FIG. 7 schematically illustrates a cross-sectional view of the distal section of the substance delivery apparatus of FIG. 3 with the balloon in a deployed configuration.

FIGS. 6 and 7 are simplified sectional views of therapeutic substance delivery assembly 338A in an undeployed and deployed arrangement, respectively. Delivery lumen 340A includes distal or first section 342 and proximal or second section 344. Distal section 342 can include overhang section 347 that extends beyond opening 341 to provide a means for securing delivery lumen 340A to balloon 320. For example, overhang section 347 can be adhered along the proximal taper wall 336 and working length 334 of balloon 320. In this manner, delivery lumen 340A is continually supported during, until, and after needle 346A is extended from delivery lumen 340A. In one embodiment, as shown in FIG. 7, delivery lumen 340A includes bend region 350 at which distal section 342 of delivery lumen 340A is capable of bending (or generally rotating) about pivotal point 351 with respect to proximal section 344. For example, to accomplish the pivotal movement, distal section 342 of delivery lumen 340A is in contact with proximal taper wall 336 of balloon 320 (FIG. 3). Accordingly, in response to the inflation of balloon 320, section 342 moves relative to section 344 to form bend region 350. In one embodiment, section 342 can move from a substantially longitudinal position to a substantially perpendicular position. Thus, the angle θ of bend region 350 can vary between 0° and 90°. In one example, after inflation of balloon 320, angle θ can range from between about 10° and 90°, for example, 45°.

Needle 346A is slidably or movably disposed in delivery lumen 340A. Needle 346A includes tissue-piercing tip 352 having dispensing port 353. Dispensing port 353 is in fluid communication with a lumen (not shown) of needle 346A. In one embodiment, the lumen of needle 346A can be pre-filled with a measured amount of a treatment agent. The lumen of needle 346A connects dispensing port 353 with treatment agent injection port 359 (FIG. 3), which is configured to be coupled to various substance dispensing means of the sort well known in the art, for example, a syringe or fluid pump. Injection port 359 allows a measured treatment agent to be dispensed from dispensing port 353 as desired or on command.

Needle 346A is coupled at proximal end 313 of catheter assembly 310 in a needle lock 355 (FIG. 3). Needle lock 355 can be used to secure needle 346A in position once needle 346A has been either retracted and/or extended from delivery lumen 340A as described below. In one embodiment, an adjustment knob 357 can be used to set the puncture distance of needle 346A as it is extended out from delivery lumen 340A and into the wall of the physiological lumen. For example, adjustment knob 357 may have calibrations, such that each revolution of the adjustment knob from one calibrated mark to another represents a fixed distance of travel for needle 346A. The portion of needle 346A protruding from delivery lumen 340 can be of any predetermined length, the specific length being dependent upon the desired depth of calibrated penetration and the procedure for which delivery assembly 338A is to be used. The protruding length of needle 346A can be from about 250 microns to about four centimeters (cm). It is appreciated that other mechanisms for securing needle 346A at a retracted or extended position may alternatively be used, including the incorporation of a mechanical stop optionally including a signaling (e.g., electrical signaling) device as described in commonly-owned U.S. patent application Ser. No. 09/746,498 (filed Dec. 21, 2000), titled "Directional Needle Injection Drug Delivery Device", and incorporated herein by reference.

Needle 346A is slidably disposed in delivery lumen 340A, so that it can move between a first retracted position (FIG. 6) and a second extended position (FIG. 7). In its first or retracted position, tissue-piercing tip 352 is located inboard of the distal surface of catheter body 312, so as to avoid damaging tissue during deployment of catheter assembly 310. In its second or extended position, tissue-piercing tip 352 is located outboard of the distal surface of catheter body 312, so as to permit needle tip 352 to penetrate the tissue surrounding the physiological passageway in which catheter assembly 310 is disposed.

Referring again to FIGS. 6 and 7, deflector 360 is disposed along an inner wall 362 of delivery lumen 340A. In one embodiment, deflector 360 includes distal section 370, medial section 372 and proximal section 374. In one embodiment, distal section 370 can be supported by delivery lumen 340A by bonding distal section 370 to overhang section 347 of delivery lumen 340A. Medial section 372 of deflector 360 can be disposed on inner wall 362 of delivery lumen 340A, such that as delivery lumen section 342 rotates relative to delivery section 344 to form bend region 350, deflector 360 is positioned over the outside of the curvature of bend region 350. Proximal section 374 exits out of delivery lumen 340A and is adhered to an outside wall 378 of delivery lumen 340A using an adhesive, such as glue or the like.

Deflector 360 can be any device that will provide a shield to protect the wall of delivery lumen 340A while being small enough, such that deflector 360 does not impact the track of catheter assembly 310 in any significant manner. In one embodiment, deflector 360 can be a ribbon member. The ribbon member can be made thin, flexible and resilient such that the ribbon member can move and bend as delivery lumen sections 342 and 344 bend and move relative to each other. Positioning deflector 360 of a ribbon member on the outside of the curvature of bend region 350 allows deflector 360 to shield the delivery lumen wall from piercing and the like by needle 346A as needle 346A moves through bend region 350. Deflector 360 also provides a surface upon which needle 346A can be made to track through bend region 350.

Deflector 360 is sized to fit into and along inner wall 362 of delivery lumen 340A without occluding or interfering with the ability of needle 346A to translate through bend region 350. For example, deflector 360 can have a thickness of between about 0.0005 inches (0.127 mm) and about 0.003 inches (0.762 mm). The width of deflector 360 may be between about 0.005 inches (1.27 mm) and about 0.015 inches (3.81 mm). The length of deflector 360 may be between about 1 cm and about 10 cm. Deflector 360 can be made from any suitable material, which allows deflector 360 to function, such as stainless steel, platinum, aluminum and similar alloy materials with similar material properties. In one embodiment, deflector 360 can be made from super-elastic alloys, such as nickel titanium alloys, for example NiTi.

Figure 10:
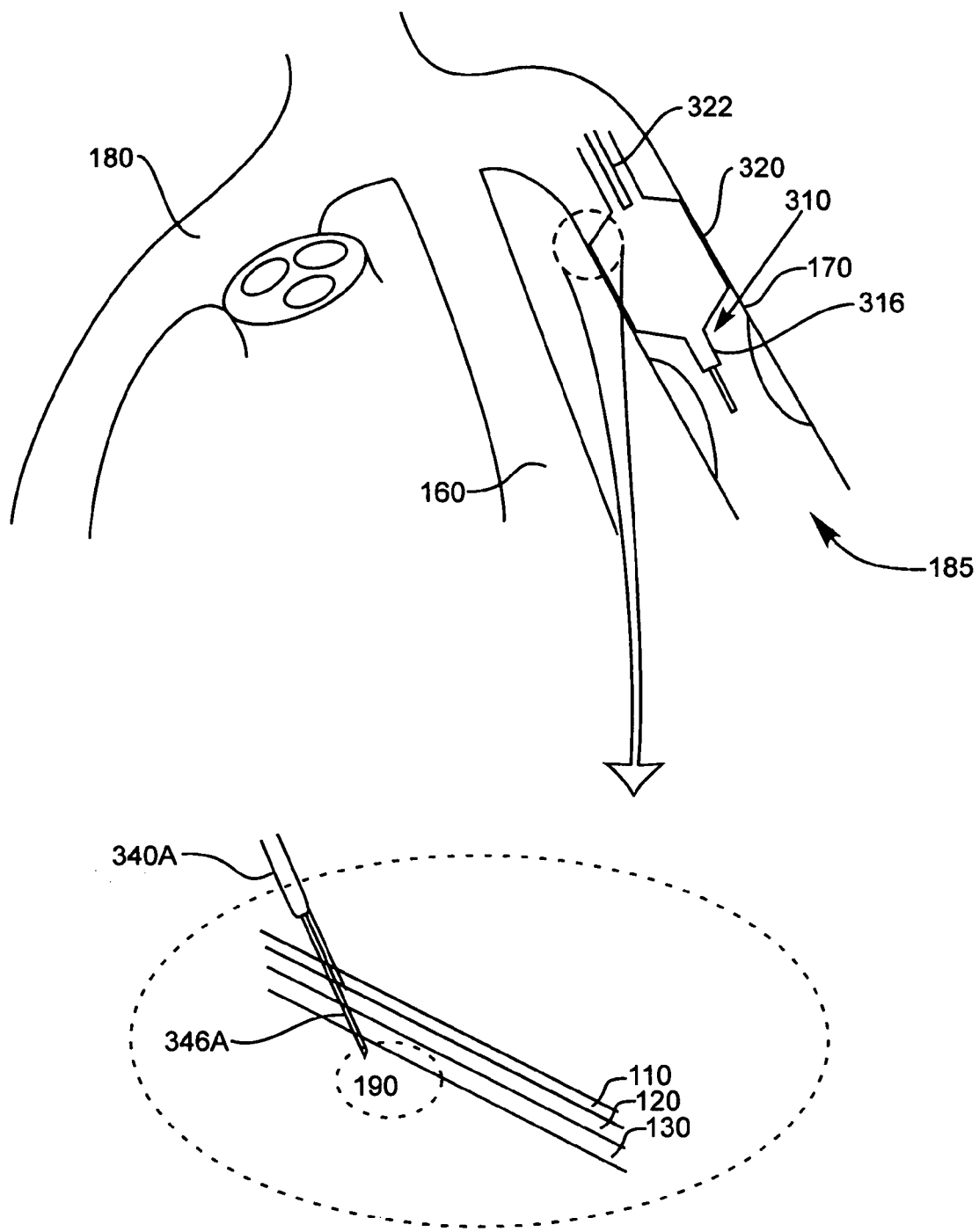
FIG. 10 schematically illustrates the left coronary artery network having a catheter assembly introduced therein.
Figure 11:
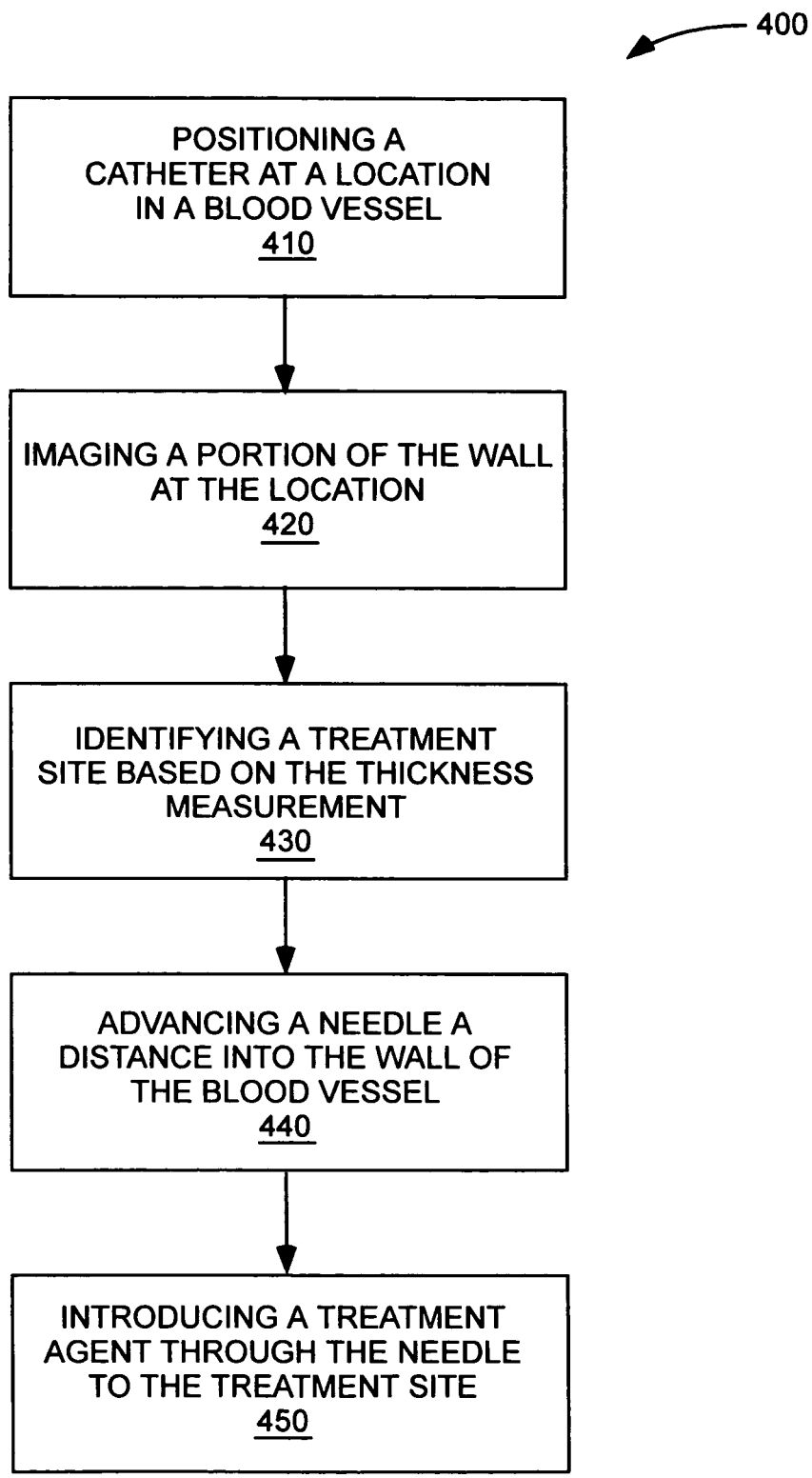
FIG. 11 presents a block diagram for introducing a treatment agent.

The catheter assembly described with reference to FIG. 3 or FIG. 9 may be used to introduce a treatment agent such as described above at a desired location. FIG. 10 illustrates one technique. FIG. 11 presents a block diagram of one technique. With reference to FIGS. 10 and 11, in a one procedure, guidewire 318 is introduced into, for example, arterial system of the patient (e.g., through the femoral artery) until the distal end of guidewire 318 is upstream of the narrowed lumen of the blood vessel (e.g., upstream of occlusion 185). Catheter assembly 300 is mounted on the proximal end of guidewire 318 and advanced over the guidewire 318 until catheter assembly 300 is position as desired. In the example shown in FIG. 10, catheter assembly 310 is positioned so that balloon 320 and delivery lumen 340a are upstream of the narrowed lumen of LCX 170 (block 410). Angiographic or fluoroscopic techniques may be used to place catheter assembly 300. Once balloon 320 is placed and subject to low inflation pressure, guidewire 318 is removed and replaced in one embodiment with an optical fiber. In the catheter assembly shown in FIG. 9, the imaging portion of an imaging device (e.g., OCT, ultrasonic, etc.) may be within the imaging lumen as the catheter is positioned. Once positioned, in this case upstream of occlusion 185, the imaging assembly is utilized to view the blood vessel and identify the various layers of the blood vessel (block 420).

The imaging assembly provides viewable information about the thickness or boundary of the intimal layer 110, media layer 120, and adventitial layer 130 of LCX 170 (See FIG. 1). The imaging assembly may also be used to measure a thickness of a portion of the blood vessel wall at the location, e.g., the thickness of the various layers of LCX 170.

LCX 170 is viewed and the layer boundary is identified or a thickness of a portion of the blood vessel wall is imaged (and possibly measured), (block 140). The treatment site may be identified based on the imaging (and possibly measuring). In one example, the treatment site is a peri-adventitial site (e.g., site 190) adjacent to LCX 170. At this point, balloon 320 is dilated as shown in FIG. 7 by, for example, delivering a liquid or gas to balloon 320 through inflation lumen 322. The inflation of balloon 320 causes needle lumen 338 to move proximate to or contact the blood vessel wall adjacent to the treatment site. Needle 346A is then advanced a distance into the wall of the blood vessel (block 140). A real time image may be used to advance needle 346A. Alternatively, the advancement may be based on a measurement of the blood vessel wall or layer boundary derived from an optical image.

In the embodiment shown in FIG. 10, needle 346A is advanced through the wall of LCX 170 to peri-adventitial site 190. Needle 346A is placed at a safe distance, determined by the measurement of a thickness of the blood vessel wall and the proximity of the exit of delivery lumen 340A to the blood vessel wall. Adjustment knob 357 may be used to accurately locate needle tip 346A in the desired peri-adventitial region. Once in position, a treatment agent, such as a treatment agent is introduced through needle 346A to the treatment site (e.g., peri-adventitial site 190).

In the above described embodiment of locating a treatment agent within or beyond a blood vessel wall (e.g., at a peri-adventitial site), it is appreciated that an opening is made in or through the blood vessel. In same instances, it may be desirable to plug or fill the opening following delivery of the treatment agent. This may be accomplished by introduction through a catheter lumen of cyanoacrylate or similar material that will harden on contact with blood.

In the above embodiment, an illustration and method was described to introduce a treatment agent at a peri-adventitial site. It is appreciated that the treatment agent may be introduced to a portion of the wall of the blood vessel. In another embodiment, the introduction is at a point beyond the media layer (e.g., beyond media layer 120 in FIG. 1) to the adventitial layer (e.g., adventitial layer 130 in FIG. 1). Further, the techniques and treatment agents described may further be used to introduce a treatment agent directly into the tissue of the myocardium.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A method comprising:
    positioning a distal portion of a delivery device at a location in a blood vessel the distal portion of the delivery device comprising a balloon and a delivery lumen coupled to an exterior surface of the balloon;
    imaging a thickness of at least a portion of a wall of the blood vessel at the location with an imaging assembly disposed in a second lumen of the delivery device;
    identifying a treatment site beyond an external elastic lamina of the blood vessel based on the imaging;
    inflating the balloon to cause a portion of the delivery lumen to pivot from a first position toward a direction of the wall of the blood vessel;

after inflating the balloon to pivot the delivery lumen, advancing a needle beyond the delivery lumen of the delivery device a distance into the wall of the blood vessel to the treatment site beyond the external elastic lamina of the blood vessel; and after advancing the needle, introducing a treatment agent in a sustained release composition through the needle.

2. The method of claim 1, wherein imaging comprises ultrasonic imaging the portion of the blood vessel wall.

3. The method of claim 1, wherein imaging comprises optical imaging the portion of the blood vessel wall.

4. The method of claim 1, wherein the treatment site comprises a peri-adventitial space.

5. The method of claim 1, wherein the treatment site comprises a site radially outward from a peri-adventitial space.

6. The method of claim 1, wherein positioning the distal portion of the delivery device comprises positioning a distal opening of the delivery lumen at a position upstream from an obstruction.

7. The method of claim 1, wherein the blood vessel is part of a network and another blood vessel in the network other than the blood vessel wherein the delivery device is positioned comprises an obstruction.

8. The method of claim 1, wherein the sustained release composition comprises a carrier.

9. The method of claim 8, wherein the carrier comprises particles having an average diameter of 10 microns or less.

10. The method of claim 8, wherein the carrier includes an opsonin-inhibitor.

11. The method of claim 1, wherein the treatment agent comprises an agent that induces an inflammation-inducing response.

12. The method of claim 11, wherein the treatment agent comprises a thermally conductive material, and the method further comprises, following introducing the treatment agent, heating the treatment agent.

13. The method of claim 1, wherein the treatment agent comprises an agent directed to a specific binding site, and wherein the treatment agent is operable to stimulate angiogenesis.

14. The method of claim 1, wherein imaging the thickness comprises imaging the thickness with optical coherence tomography.

15. The method of claim 1, wherein the imaging comprises imaging through the balloon.

16. The method of claim 15, wherein the imaging through the balloon comprises imaging through a transparent material of the balloon.

17. The method of claim 1, wherein the treatment agent comprises a non-specific treatment agent operable to induce inflammation.

18. The method of claim 1, wherein the treatment agent comprises at least one selected from sol gel particles, calcium phosphate glass comprising iron, fibrin, gelatin, low molecular weight hyaluronic acid, chitin, bacterial polysaccharides, and metal particles.

19. The method of claim 1, further comprising deflecting the needle with a ribbon member deflector.

20. The method of claim 1, further comprising:
measuring the thickness of the portion of the wall of the blood vessel using the imaging assembly; and
identifying the treatment site based on the imaging and measuring.

21. A method comprising:
positioning a distal portion of a delivery device at a location in a blood vessel the distal portion of the delivery device coupled to an exterior surface of a balloon;
imaging a thickness of at least a portion of a wall of the blood vessel at the location with an imaging assembly disposed in a lumen of the delivery device;
pivoting the distal portion of the delivery device from a first position toward the portion of the wall of the blood vessel by inflating the balloon;
after pivoting the distal portion of the delivery device, advancing a needle beyond the distal portion of the delivery device a distance into the wall of the blood vessel to a treatment site beyond an external elastic lamina of the blood vessel; and
after advancing the needle, introducing a treatment agent through the needle,
wherein the treatment agent comprises an inflammation-inducing agent.

22. The method of claim 21, wherein the treatment agent comprises an agent directed to specific binding sites that is operable to stimulate angiogenesis.

23. The method of claim 21, wherein the treatment agent comprises carrier particles including the inflammation-inducing agent and having a sustained-release property within a physiological setting.

24. The method of claim 21, wherein the inflammation-inducing agent comprises at least one of a sol-gel particle, a silica particle, a glass including iron, chitin, fibrin, bacterial polysaccharides, vaccines, and particles of metal.

25. The method of claim 21, wherein the inflammation-inducing agent comprises at least one of a polycaprolactone, a polyhydroxybutyrate-valerate, a poly(oxy)ethylene, a polyurethane, and a silicone.

26. The method of claim 21, wherein the treatment agent comprises carrier particles including the inflammation-inducing agent, and wherein the carrier particles comprise at least one selected from poly (L-lactide), poly (D,L-lactide), poly (glycolide), poly (lactide-co-glycolide), polycaprolactone, polyanhydride, polydiaxanone, polyorthoester, polyamino acids, poly (trimethylene carbonate), and combinations thereof.

27. The method of claim 21, wherein the imaging comprises imaging through the balloon disposed at the distal portion of the delivery device.

28. The method of claim 27, wherein the imaging through the balloon comprises imaging through a transparent material of the balloon.

29. The method of claim 21, wherein the treatment agent comprises a non-specific treatment agent.

30. The method of claim 21, wherein the treatment agent comprises at least one selected from sol gel particles, calcium phosphate glass having iron, fibrin, gelatin, low molecular weight hyaluronic acid, chitin, bacterial polysaccharides, and metal particles.

31. The method of claim 21, further comprising deflecting the needle with a ribbon member deflector.

32. The method of claim 21, wherein the imaging comprises imaging with optical coherence tomography.

* * * * *